(12) United States Patent
Ding et al.

(10) Patent No.: US 11,193,167 B2
(45) Date of Patent: Dec. 7, 2021

(54) MULTIPLEX PYROPHOSPHOROLYSIS ACTIVATED POLYMERIZATION TO AMPLIFY MULTIPLE ALMOST-SEQUENCE-IDENTICAL TEMPLATES IN A SINGLE REACTION

(71) Applicants: Shaofeng Ding, Santa Fe Springs, CA (US); Qiang Liu, Rancho Cucamonga, CA (US)

(72) Inventors: Shaofeng Ding, Santa Fe Springs, CA (US); Tony Zhou Lee, San Diego, CA (US); Qiang Liu, Rancho Cucamonga, CA (US)

(*) Notice: Subject to any disclaimer, the term of this patent is extended or adjusted under 35 U.S.C. 154(b) by 0 days.

(21) Appl. No.: 16/408,442

(22) Filed: May 9, 2019

(65) Prior Publication Data
US 2019/0271035 A1 Sep. 5, 2019

Related U.S. Application Data

(63) Continuation-in-part of application No. 15/462,342, filed on Mar. 17, 2017, now Pat. No. 10,513,727.

(51) Int. Cl.
C12Q 1/6853 (2018.01)
C12Q 1/6858 (2018.01)
C12Q 1/6848 (2018.01)

(52) U.S. Cl.
CPC ......... *C12Q 1/6853* (2013.01); *C12Q 1/6848* (2013.01); *C12Q 1/6858* (2013.01)

(58) Field of Classification Search
CPC .. C12Q 1/6858; C12Q 1/6848; C12Q 1/6853; C12Q 2537/143
See application file for complete search history.

(56) References Cited

U.S. PATENT DOCUMENTS

2009/0263811 A1* 10/2009 Kiyohara ............. C12Q 1/6858
435/6.11

OTHER PUBLICATIONS

Liu et al., "An improved allele-specific PCR primer design method for SNP marker analysis and its application," Plant Methods, vol. 8, No. 34, pp. 1-9. (Year: 2012).*
Liu et al., "Multiplex dosage pyrophosphorolysis-activated polymerization: application to the detection of heterozygous deletions," BioTechniques, vol. 40, No. 5, pp. 661-668. (Year: 2006).*
Guo et al., "Enhanced Discrimination of single nucleotide polymorphisms by artificial mismatch hybridization," Nature Biotechnology, vol. 15, pp. 331-335. (Year: 1997).*
Kinzler et al., "Identification of FAP Locus Genes from Chromosome 5q21," Science, August, vol. 253, No. 5020, pp. 661-665. (Year: 1991).*
Okimoto et al, "Improved PCR Amplification of Multiple Specific Allels (PAMSA) Using Internally Mismatched Primers," BioTechniques, July, vol. 21, No. 1, pp. 20-26. (Year: 1996).*
Kwok et al., "Effects of primer-template mismatches on the polymerase chain reaction: Human immunodeficiency virus type 1 model studies," Nucleic Acids Research, vol. 18, No. 4, pp. 999-1005. (Year: 1990).*

* cited by examiner

*Primary Examiner* — Young J Kim

(57) ABSTRACT

Multiplex pyrophosphorolysis activated polymerization uses multiple pairs of blocked primers to amplify multiple potential templates in a single reaction, including those almost-sequence-identical templates located in one locus. To identify and differentiate the multiple amplified products, individual molecules are sequenced in parallel. Thus multiplex PAP amplification is combined with parallel sequencing for ultrahigh-sensitive, ultrahigh-selective and ultrahigh-throughput detection of early cancer.

11 Claims, 6 Drawing Sheets

Specification includes a Sequence Listing.

|  | Complementarities | No. mismatch |
|---|---|---|
| COSM 6255 template { | COSM 6255 primer    5'AGTGAACATTCC..><br>Starting template    3'tcaattttaaggg....5' | 2 |
| | COSM 6255 primer    5'AGTGAACATTCC..≥<br>Duplicated template 3'tcaCttGtaaggg....5' | 0 |
| | COSM12369 primer    5'AGGTACAATTCC..><br>Starting template    3'tcaattttaaggg....5' | 2 |
| | COSM12369 primer    5'AGGTACAATTCCCGT..><br>Duplicated template 3'tcaCttGtaagggca....5' | 4 |

Figure 1

|  | Complementarities | No. mismatch |
|---|---|---|

COSM 6252 template
{
COSM 6252 primer     5' ACTGCATTCAAA..>           1
Starting template    3' tgacTtaagtttt....5'

COSM 6252 primer     5' ACTGCATTCAAA..>           0
Duplicated template  3' tgacGtaagtttt....5'

COSM 6253 primer     5' ACTGAAGTCAAA..>           1
Starting template    3' tgactTaagtttt....5'

COSM 6253 primer     5' ACTGAAGTCAAA..>           2
Duplicated template  3' tgacGtaagtttt....5'

COSM 6239 primer      5' CTGAATGCAAA..>           1
Starting template     3' tgactTaagtttt....5'

COSM 6239 primer      5' CTGAATGCAAA..>           2
Duplicated template   3' tgacGtaagtttt....5'
}

Figure 3

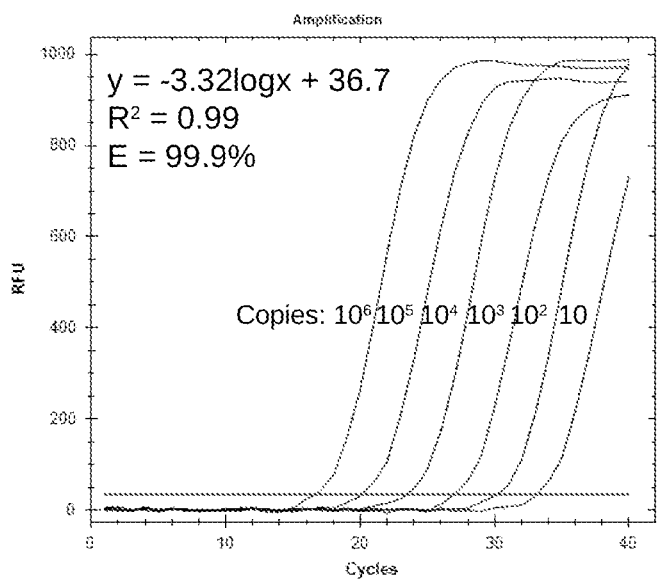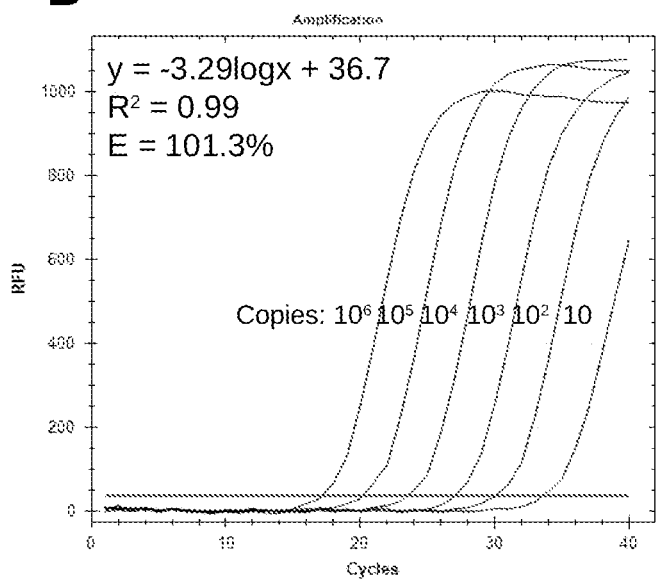
Figure 4

Complementarities   No. mismatch

COSM 518 template {

COSM 518 primer　　　5' CTGACTATAAAC..>　　　1
Starting template　　3' gacttatatttga....5'

COSM 518 primer　　　5' CTGACTATAAAC..>　　　0
Duplicated template　3' gactGatatttga....5'

COSM 516 primer　　　5' CTGAATCTAAAC..>　　　1
Starting template　　3' gacttatatttga....5'

COSM 516 primer　　　5' CTGAATCTAAAC..>　　　2
Duplicated template　3' gactGatatttga....5'

COSM 517 primer　　　5' CTGAATATCAAC..>　　　1
Starting template　　3' gacttatatttga....5'

COSM 517 primer　　　5' CTGAATATCAAC..>　　　2
Duplicated template　3' gactGatatttga....5'

Figure 5

MULTIPLEX PYROPHOSPHOROLYSIS ACTIVATED POLYMERIZATION TO AMPLIFY MULTIPLE ALMOST-SEQUENCE-IDENTICAL TEMPLATES IN A SINGLE REACTION

CROSS-REFERENCE TO RELATED APPLICATIONS

This CIP application claims priority from U.S. non-provisional patent application Ser. No. 15/462,342, filed on Mar. 17, 2017.

SEQUENCE LISTING

This application is being filed along with a Sequence Listing and its electronic format entitled SequenceListing.txt.

BACKGROUND OF THE INVENTION

Field of the Invention

The present invention relates to the field of molecular biology and particularly pyrophosphorolysis activated polymerization (PAP) for nucleic acid amplification.

Description of the Prior Art

PAP Technology for Nucleic Acid Amplification

Pyrophosphorolysis activated polymerization (PAP) is a method for nucleic acid amplification where pyrophosphorolysis and polymerization are serially coupled by DNA polymerase using 3' blocked primers (Liu and Sommer, 2000; Liu and Sommer, 2004b). A primer is blocked at the 3' end with a non-extendable nucleotide (3' blocker), such as a dideoxynucleotide, and cannot be directly extended by DNA polymerase. When the 3' blocked primer anneals to its complementary DNA template, DNA polymerase can remove the 3' blocker from the 3' blocked primer in the presence of pyrophosphate or its analog, which reaction is called pyrophosphorolysis. The DNA polymerase can then extend the 3' unblocked primer on the DNA template. In addition to references cited herein, PAP has been described in U.S. Pat. Nos. 6,534,269, 7,033,763, 7,105,298, 7,238,480, 7,504,221, 7,914,995, and 7,919,253.

The serial coupling of pyrophosphorolysis and extension using the 3' blocked primer in PAP results in an extremely high selectivity (Liu and Sommer, 2004a; Liu and Sommer, 2004b) because a significant nonspecific amplification (Type II error) requires mismatch pyrophosphorolysis followed by mis-incorporation by the DNA polymerase, an event with a frequency estimated to be $3.3 \times 10^{-11}$.

The bi-directional form of PAP (Bi-PAP) is especially suitable for allele-specific amplification that uses two opposing 3' blocked primers with a single nucleotide overlap at their 3' ends (Liu and Sommer, 2004a; Liu and Sommer, 2004b). Bi-PAP can detect one copy of a mutant allele in the presence of $10^9$ copies of the wild type DNA without false positive amplifications.

DNA-PAP

PAP was initially tested with Tfl and Taq polymerases using DNA template of the human dopamine D1 gene, proving the principle that DNA-dependent DNA pyrophosphorolysis and DNA-dependent DNA polymerization can be serially coupled (Liu and Sommer, 2000). The efficiency of PAP was greatly improved using TaqFS, a genetically engineered polymerase comprising a F667Y mutation, which were demonstrated using other DNA templates (Liu and Sommer, 2002).

RNA-PAP

RNA-PAP was developed that can directly amplify RNA template without additional treatment. RNA-PAP brings in a new mechanism for amplification of RNA template in which RNA-dependent DNA pyrophosphorolysis removes 3' blocker such as 3' dideoxynucleotide from a blocked primer when hybridized to RNA template, and then RNA-dependent DNA polymerization extends the activated primer. Due to this serial coupling, RNA-PAP has high selectivity against mismatches on the RNA template, providing highly specific amplification of RNA template (U.S. Pat. No. 9,133,491).

PAP with Acycolonucleotide Blocker and Type II Polymerase

We showed that Type II DNA polymerase efficiently catalyzes template-dependent pyrophosphorolysis to activate primers blocked at their 3' termini with acyclonucleotides in which a 2-hydroxyethoxymethyl group substitutes for the 2'-deoxyribofuranosyl sugar. Type II DNA polymerases Vent (exo-) and Pfu (exo-) were used for PAP with acyclonucleotide-blocked primers, besides Type I DNA polymerase (Liu and Sommer, 2004c).

Multiplex-PAP at Multiple Loci: Multiple Pairs of Primers Amplify Multiple Templates at Multiple Loci Advantageous to produce little or no primer-dimer or false priming (Liu and Sommer, 2002), multiple pairs of primers (≥2) were used to amplify multiple potential templates (≥2) located at mutiple loci (≥2) in one reaction (Liu, et al., 2006). In an example, PAP used eight pairs of primers that targeted eight loci in human genome including seven different exons scattered along a 30 Kb sequence of the human factor IX gene and one exon in the human ATM gene.

Inhibitory Interaction in One-Locus-Duplex-PAP: Multiple Pairs of Primers Amplify Multiple Almost-Sequence-Identical Templates at One Locus We developed many Singleplex-PAP assays for detection of A/T biallelic polymorphisms in human genome, such as Rs4261 and Rs31224 loci. Each polymorphism contains an A or a T nucleotide exactly at the same nucleotide (Table 1).

For the biallelic polymorphism Rs4261, the first pair of blocked primers (SEQ ID No 2 and 3) were regularly designed as 5'-perfect-match primers, which match the A allelic template (SEQ ID 1), but mismatch the T allelic template at the 3' ends (SEQ ID 4) (Table 1). The Singleplex-PAP amplified the A allelic template, but extremely discriminated against the T allelic template.

The second pair of blocked primers (SEQ ID No 5 and 6) were also regularly designed as 5'-perfect-match primers, which match the T allelic template (SEQ ID 4), but mismatch the A allelic template at the 3' ends (SEQ ID 1). The Singleplex-PAP amplified the T alleleic template (SEQ ID 4), but did not amplify the A allelic template (SEQ ID 1) at all.

The amplification efficiency of each Singleplex-PAP was measured to be >96% in serial dilution experiments in which the genomic template DNA was 10-fold serially diluted from $10^6$ to 10 copies per 20 ul of reaction.

However, when the two pairs of primers (SEQ ID No 2 and 3, 5 and 6), put together in one reaction, to amplify either or both of the two allelic templates (SEQ ID 1 and 4), the One-Locus-Duplex-PAP produced much less corresponding products with the amplification efficiencies 85-87%, leading to 16-fold less products by the end of the 30th cycle, thus indicating inhibitory interaction between the primers.

In another example of the biallelic polymorphism Rs4261, two pairs of blocked primers (SEQ ID No 8 and 9, 11 and 12) were regularly designed as 5'-perfect-match primers for the A and T alleles (SEQ ID 7 and 10) (Table 1). Similar tendencies of the inhibitory interaction were observed in amplification efficiencies, about 10% decreases per cycle between the Singleplex-PAP and One-Locus-Duplex-PAP.

With regularly designed 5'-perfect-match primers, this inhibitory interaction is common in One-Locus-Duplex-PAP. We hypothesize that competitive annealing of multiple almost-sequence-identical primers to their multiple almost-sequence-identical templates leads to the inhibition.

Advantages of the Invention of One-Locus-Multiplex-PAP

In order to amplify multiple potential almost-sequence-identical templates or alleles at one locus, a new design was developed that artificial mutations were introduced into multiple pairs of primers to reduce the inhibitory interaction and thus increase the amplification efficiencies.

SUMMARY OF THE INVENTION

A plurality of pairs of forward and reverse blocked primers for pyrophosphorolysis activated polymerization amplify a plurality of potential templates in one reaction, in which the templates are located at one locus in a genome and have at least one nucleotide variance from each other.

The plurality of pairs of forward and reverse blocked primers comprise: 1) a first pair of forward and reverse primers to amplify a first template, in which the forward primer or reverse primer has at least one artificial mutation introduced into its 5' region, and 2) a second pair of forward and reverse primers to amplify a second template, in which the second forward or reverse primer in the same direction as the above 5' mutated primer in the first pair has at least one artificial mutation introduced into its 5' region, and in which the artificial mutations of the 5' mutated primers in the first pair and in the second pair are located at different nucleotides at the locus of the genome.

A method for multiplex PAP comprises: a) providing a plurality of pairs of forward and reverse blocked primers to amplify a plurality of potential templates in one reaction, in which the templates are located at one locus in a genome and have at least one nucleotide variance from each other, comprising: 1) a first pair of forward and reverse primers to amplify a first template, in which the first forward primer or reverse primer has at least one artificial mutation introduced into its 5' region, and 2) a second pair of forward and reverse primers to amplify a second template, in which the second forward or reverse primer in the same direction as the above 5' mutated primer in the first pair has at least one artificial mutation introduced into its 5' region, in which the artificial mutations of the 5' mutated primers in the first pair and in the second pair are located at different nucleotides at the locus of the genome, and b) amplifying the templates in one reaction.

The method for multiplex PAP further comprise a step c) sequencing individual molecules of the multiple amplified products in parallel.

Of the method for multiplex PAP, the plurality of pairs of forward and reverse blocked primers further comprise a third pair of forward and reverse primers to amplify a third template, in which the third forward or reverse primer in the same direction as the above 5' mutated primer in the first and second pairs has at least one artificial mutation introduced into its 5' region, in which the artificial mutations of the 5' mutated primers in the first pair, the second pair and the third pair are located at different nucleotides at the locus of the genome.

Of the method for multiplex PAP, the plurality of pairs of forward and reverse blocked primers comprise: 1) the first pair of forward and reverse primers, in which the other primer in the first pair has at least one artificial mutation introduced into the 5' region, and 2) the second pair of forward and reverse primers, in which the other primer in the second pair has at least one artificial mutation introduced into the 5' region, in which the artificial mutations of the 5' mutated primers in the first pair and the second pair are located at different nucleotides at the locus of the genome.

Of the method for multiplex PAP, the 3' regions of the first pair of primers match the first template but mismatch the second template, and the 3' regions of the second pair of primers match the second template but mismatch the first template, and in which the first and second templates are located at the same locus but contain at least one nucleotide variance from each other.

Of the method for multiplex PAP, one or two artificial mutations are introduced into the 5' region of the first forward or reverse primer, whereby the 5' region substantially but not completely matches its template.

Of the method for multiplex PAP, one or two artificial mutations are introduced into the 5' region of the second forward or reverse primer, whereby the 5' region substantially but not completely matches its template.

Of the method for multiplex PAP, the artificial mutation of the 5' mutated primer in each of the first and second pairs is selected from the group consisting of six types of A to C, C to A, T to G, G to T, A to T, and T to A mutations.

Of the method for multiplex PAP, the artificial mutation of the 5' mutated primer in each of the first and second pairs result in one of the four types of mismatches of G-A, C-T, A-A, and T-T between the 5' region of the 5' mutated primer and the complementary strand of the template.

Of the method for multiplex PAP, the artificial mutation of the 5' mutated primer in any of the first and second pairs is selected from the group consisting of four types of A to C, C to A, T to G, and G to T mutations.

Of the method for multiplex PAP, the artificial mutation of the 5' mutated primer in any of the first and second pairs is selected from the group consisting of two types of A to T and T to A mutations.

Of the method for multiplex PAP, the 5' regions of the 5' mutated primers in the first and second pairs range from the first to the twelfth nucleotide from the 5' ends, including the nucleotides at the 5' ends assigned as the first nucleotides from the 5' ends.

Of the method for multiplex PAP, the artificial mutations of the 5' mutated primers in the first and second pairs are at different nucleotides at the locus in the genome.

Of the method for multiplex PAP, the first and second templates are completely or partially overlapped in the locus.

Of the method for multiplex PAP, the first and second templates contain at least one nucleotide variance from each other but are located at the same locus in the genome.

BRIEF DESCRIPTION OF THE DRAWINGS

FIG. 1 shows how 5'-artificial-mismatch blocked primers work in One-Locus-Duplex-PAP in exon 19 of the EGFR gene. In the example, two pairs of primers were designed as 5'-artificial-mismatch primers COSM6255 and COSM12369 (SEQ ID No 15 and 16, 19 and 16) (Table 2).

Only the 5' regions of the forward primers (SQE ID 15 and 19) are diagramed with the complementary strands of the starting and duplicated templates COSM6255 (SEQ ID 13 and 14). Underlined and upper cases in the primer sequences are the artificial mutations. Underlined and upper cases in the duplicated templates are artificial mutations duplicated from the 5'-artificial-mismatch primers. The mismatch between the 5' region of a primer and the complementary strand of a template is indicated by rectangle frame. The number of mismatches is indicated for each case on the right side, showing different levels of complementarities.

Figure 2:
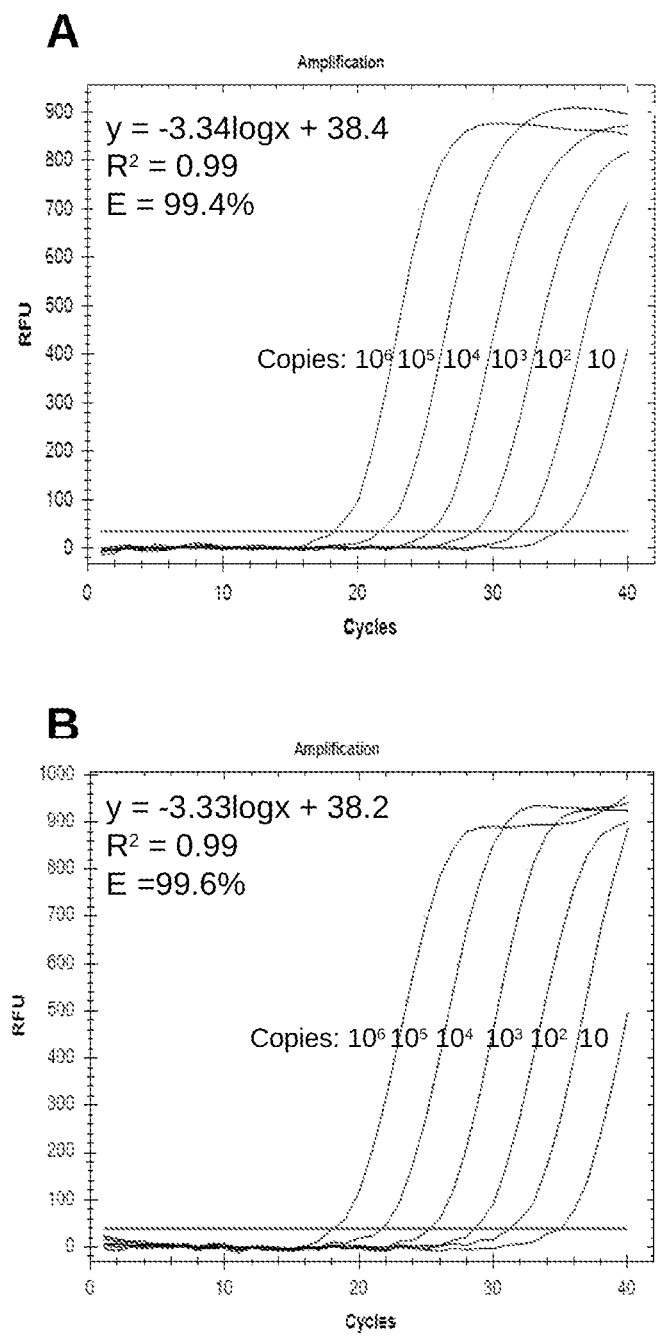

FIG. 2 shows comparison of amplification efficiencies in exon 19 of the EGFR gene. In panel A, Singleplex-PAP used a pair of 5'-artificial-mismatch blocked primers COSM6255 (SEQ ID No 15 and 16) to amplify the templates COSM6255 (SEQ ID 13 and 14) form plasmid DNA (Table 2). In panel B, One-Locus-Duplex-PAP used two pairs of primers COSM6255 and COSM12369 (SEQ ID No 15 and 16, 19 and 16) to amplify the templates COSM6255 (SEQ ID 13 and 14) form plasmid DNA. To determine the amplification efficiency, the template was 10-fold serially diluted from $10^6$ to 10 copies per 20 ul of reaction. Threshold line is also indicated. X-axis is the cycle number and Y-axis is the net fluorescence signal in arbitrary units. Amplification efficiencies of the Singleplex-PAP and One-Locus-Duplex-PAP were determined together with equations of linear regression and coefficients of determination ($R^2$) by plotting Ct values versus log DNA copies.

FIG. 3 shows how 5'-artificial-mismatch primers work in One-Locus-Triplex-PAP in exon 18 of the EGFR gene. In the example, three pairs of primers were designed as 5'-artificial-mismatch primers COM6252, COSM6253 and COSM6239 (SEQ ID 22 and 23, 26 and 27, 30 and 31) (Table 4). Only the 5' regions of the forward primers (SEQ ID 22, 26 and 30) are diagramed with the complementary strands of the starting and duplicated templates COM6252 (SEQ ID 20 and 21).

FIG. 4 shows comparison of amplification efficiencies in exon 18 of the EGFR gene. In panel A, Singleplex-PAP used a pair of 5'-artificial-mismatch blocked primers COSM6252 (SEQ ID 22 and 23) to amplify the templates COSM6252 (SEQ ID 20 and 21) form plasmid DNA (Table 4). In panel B, One-Locus-Triplex-PAP used three pairs of primers COSM6252, COSM6253 and COSM6239 (SEQ ID 22 and 23, 26 and 27, 30 and 31) to amplify the templates COSM6252 (SEQ ID 20 and 21) form plasmid DNA.

FIG. 5 shows how 5'-artificial-mismatch primers work in One-Locus-Triplex-PAP in exon 2 of the KRAS gene. In the example, three pairs of primers were designed as 5'-artificial-mismatch primers COSM518, COSM516 and COSM517 (SEQ ID 34 and 35, 38 and 39, 42 and 43) (Table 6). Only the 5' regions of the forward primers (SEQ ID 34, 38 and 42) are diagramed with the complementary strands of the starting and duplicated templates COSM 518 (SEQ ID 32 and 33).

Figure 6:
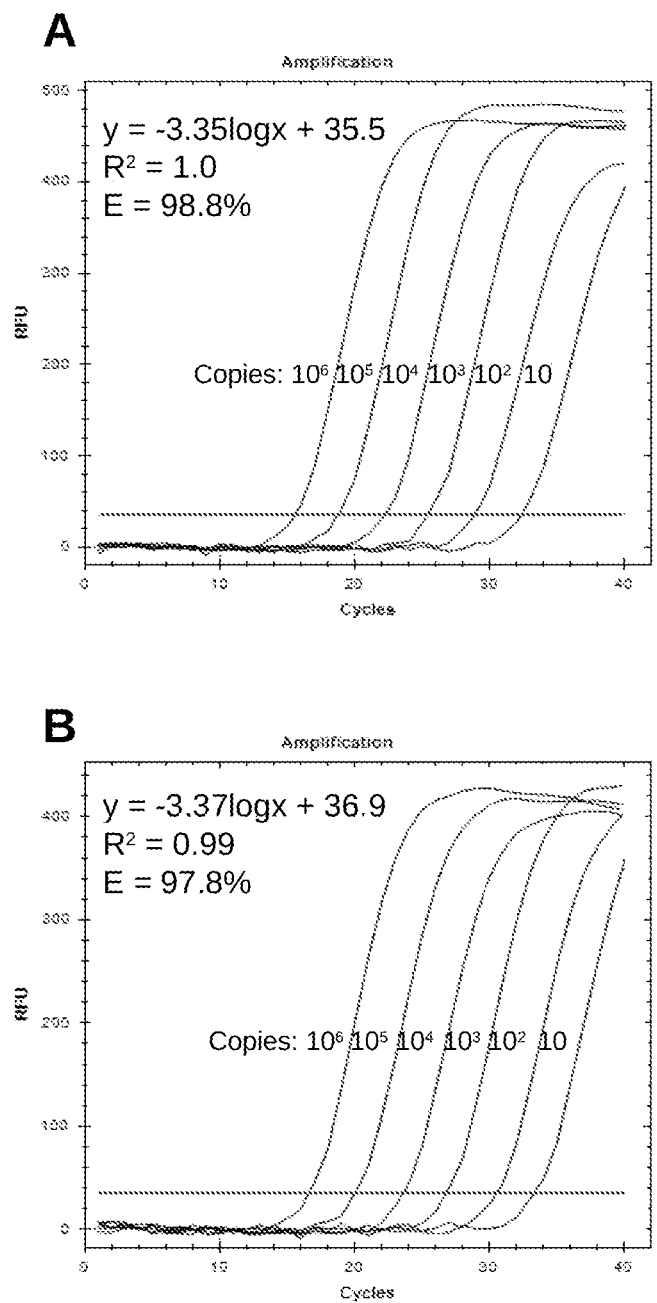

FIG. 6 shows comparison of amplification efficiencies in exon 2 of the KRAS gene. In panel A, Singleplex-PAP used a pair of 5'-artificial-mismatch blocked primers COSM518 (SEQ ID 34 and 35) to amplify the templates COSM518 (SEQ ID 32 and 33) from plasmid DNA (Table 6). In pane B, One-Locus-Triplex-PAP used three pairs of primers COSM518, COSM516 and COSM517 (SEQ ID 34 and 35, 38 and 39, 42 and 43) to amplify the template COSM518 form plasmid DNA (SEQ ID 32 and 33).

DETAILED DESCRIPTION OF THE INVENTION

Terminology

Unless defined otherwise, all technical and scientific terms used herein have the same meaning as commonly understood by one of ordinary skill in the art.

PCR refers to polymerase chain reaction.

Pyrophosphorolysis is the reverse reaction of deoxyribonucleic acid polymerization. In the presence of pyrophosphate, the 3' nucleotide is removed by a polymerase from duplex DNA to generate a triphosphate nucleotide and a 3' unblocked duplex DNA: $[dNMP]_n + PPi \rightarrow [dNMP]_{n-1} + dNTP$ (Deutscher and Kornberg, 1969).

Polymerase or nucleic acid polymerase refers to a polymerase characterized as polymerization or extension of deoxyribonucleic acids.

3' blocked primer refers to an oligonucleotide with a 3' non-extendable nucleotide (3' blocker), such as a dideoxynucleotide or an acycolonucleotide. The 3' nucleotide could not be directly extended, but it can be removed by pyrophosphorolysis and then the unblocked primer can be extended by polymerase.

PAP refers to pyrophosphorolysis activated polymerization.

Bidirectional-PAP (Bi-PAP) is a form of PAP that uses a pair of opposing blocked primers that overlap by one nucleotide at their 30 termini.

Exponential-PAP is a form of PAP that uses a pair of two opposing forward and reverse primers for exponential product accumulation with cycles. At least one primer is blocked primer.

Sensitivity or detection limit is defined as the smallest copy number of a template that generates a detectable product when the blocked primers match the template at the targeted nucleotide, such as the 3' end.

Specificity is defined as the largest copy number of a template that generates an undetectable product when the blocked primers mismatch the template at the targeted nucleotide, such as the 3' end.

Selectivity, the ratio of sensitivity to specificity, is defined as the ability to detect a small number of copies of the matched template in the presence of a large number of copies of mismatched templates without causing false positives.

Thermostable enzyme refers to an enzyme that is heat stable or heat resistant.

TaqFS is a genetic engineered form of Taq polymerase containing G46E and F667Y amino acid changes compared with wild type sequence.

A locus is defined as a short region of nucleotide sequence, such as 40 bp, in genome.

Multiple templates or alleles at one locus mean that at least two templates are located at a short region of nucleotide sequence. The sequence differences among the templates, may be as little as one base substitution, a few base deletion or insertion, and may be located as near as at the same nucleotide. In addition, the alleles may be completely or partially overlapped within the region.

Multiple almost-sequence-identical templates or alleles mean at least two templates, typically located at one locus in genome, among which the sequence differences may be as little as one base substitution, a few base deletion or insertion.

A pair of primers means two opposing forward and reverse primers.

Singleplex-PAP means that one pair of primers amplify one template in a reaction.

Multiplex-PAP means that ≥2 pairs of primers amplify ≥2 potential templates in a reaction.

Multiplex-PAP at multiple loci is a form of multiplex PAP that ≥2 pairs of primers amplify ≥2 potential templates at ≥2 loci in a reaction.

One-Locus-Multiplex-PAP is a form of multiplex PAP that ≥2 pairs of primers amplify ≥2 potential templates at one locus in a reaction.

One-Locus-Duplex-PAP means that 2 pairs of primers amplify 2 potential templates at one locus in a reaction.

One-Locus-Triplex-PAP means that 3 pairs of primers amplify 3 potential templates at one locus in a reaction.

The 5' region of a primer is the 5' part of the primer sequence, such as the ten successive nucleotides from the 5' end.

The 3' region of a primer is the 3' part of the primer sequence, such as the ten successive nucleotides from the 3' end.

Central region of a primer is the middle part of the primer sequence between the 5' region and the 3' region.

5'-perfect-match primer: the 5' region has no artificial mutations and perfectly matches the starting template.

5'-artificial-mismatch primer: artificial mutations are introduced into the 5' region, resulting to mismatch to the starting template.

5' mutated primer: i.e., 5'-artificial-mismatch primer, artificial mutations are introduced into the 5' region.

Artificial mutation means the mutation that is artificially introduced into primer sequences for substitution, typically in the 5' region.

Artificial mismatch is formed between the artificial mutation in the 5' region of 5'-artificial-mismatch primer and the template.

Starting template is the original template before amplification starts, such as that from genomic or plasmid DNA template.

Duplicated template is duplicated from the starting template in amplification and can also be taken as template in later cycles.

Terminology of Real-Time Fluorescence Detection

Baseline is the level of fluorescence signal during initial cycles. The low level can be considered as background or "noise" of the reaction.

Threshold is defined as the level of fluorescence signal that is a significant higher than baseline signal and can distinguish amplification signal from the background.

Ct (threshold cycle) is the cycle number at which the fluorescence signal crosses the threshold.

Amplification efficiency is defined as the percent of template that is amplified by the end of a cycle.

Principle of 5'-Artificial-Mismatch Primers for One-Locus-Multiplex-PAP

In order for multiple pairs of blocked primers to amplify multiple almost-sequence-identical templates or alleles at one locus without inhibitory interaction, a novel design of 5'-artificial-mismatch primers was developed that contain artificial mutations in the 5' regions, as in Examples 2-4.

a) Four Types of Artificial Mismatches Preferred

Mismatches in short DNA duplexes significantly reduce their thermal stabilities, the levels depending on the type of mismatches. The order of thermal stabilities of a total of eight possible mismatches are approximately: G-T>G-G>G-A>C-T>A-A=T-T>A-C=C-C (mismatch G-T=T-G, G-A=A-G, C-T=T-C, and A-C=C-A) (Modrich, 1987) (Aboul-ela, et al., 1985) (Ikuta, et al., 1987).

We prefer four types of mismatches of G-A, C-T, A-A and T-T because 1) their thermal stabilities are medium in the order: they can disrupt the structures of short DNA duplexes, the levels being not too little and not too much, and 2) their thermal stabilities are within a successive range in the order.

b) The Four Types of Mismatches Caused by Six Types of Artificial Mutations

Considering a One-Locus-Multiplex-PAP, at least two pairs of primers are applied to at least two potential templates. We chose six types of artificial mutations of A to C and C to A, T to G and G to T, A to T and T to A in primers, which always lead to the four types of artificial mismatches between the primers and the complementary strands of the starting or duplicated templates. The other six possible types of artificial mutations of A to G and G to A, T to C and C to T, G to C and C to G are not used at all in the design.

The A to C or C to A artificial mutations cause two types of mismatches of C-T and A-G (mismatch C-T=T-C, and A-G=G-A) between the primers and the complementary strands of the starting or duplicated templates. The T to G and G to T artificial mutations cause the same two types of mismatches of G-A and T-C (mismatch G-A=A-G, and T-C=C-T) between the primers and the complementary strands of the starting or duplicated templates. The A to T and T to A artificial mutations cause other two types of mismatches of T-T and A-A between the primers and the complementary strands of the starting or duplicated templates. Thus, a total of four types of mismatches are counted in One-Locus-Multiplex-PAP.

c) The Number of Artificial Mismatches Caused by Artificial Mutations

When artificial mutations of the forward or reverse primers are designed at different nucleotides in the templates, the number of mismatches between the 5' region of a primer and the complementary strand of a starting or duplicated template depends on the number of artificial mutations of the primer and on the template. In any case, the minimum number of mismatches between the 5' region of a primer and the complementary strand of a duplicated template is zero, such as in Examples 2-4.

d) Locations of Artificial Mismatches Preferred to Localize in the 5' Region of Primers We prefer to localize artificial mismatches in the 5' regions of primers because 1) besides the types, the locations of mismatches also affect thermal stability of short DNA duplexes (Modrich, 1987) (Piao, et al., 2008), and 2) We found that 28-30mer blocked primers commonly had >90% efficiency of pyrophosphorolysis and extension when mismatches vary from the $1^{st}$ to $12^{th}$ nucleotides from the 5' ends, i.e., the 5' regions. However, they had very low efficiency of pyrophosphorolysis and extension when mismatches are located in the 3' regions, particularly at the 3' ends.

Thus, artificial mutations are preferred to localize in the 5' regions, ranging from the $1^{st}$ to the $12^{th}$ nucleotide from the 5' ends, better ranging from the $3^{rd}$ to $9^{th}$ nucleotide from the 5' ends.

e) Mechanism by Different Numbers of Mismatches Between Different Primers and Different Templates in One-Locus-Multiplex-PAP In a One-Locus-Multiplex-PAP, ≥2 pairs of primers amplify ≥2 potential templates at one locus in a reaction. For a 5'-artificial-mismatch primer, such as each of the forward primers of the first pair, the second pair and the third pair, an artificial mutation is designed into the 5' region. The number of mismatches between the 5' regions and the complementary strands of the starting or duplicated templates varies, such as from zero to 4, depending on annealing of a specific primer to a specific template. Thus, the different numbers of mismatches between different primers and different templates provide the mechanism to reduce inhibitory interaction: 1) the 5' region of a 5'-atifitial-mismatch primer matches its corresponding templates more than its competing templates, and 2) a template matches the 5' region of its corresponding 5'-atifitial-mismatch primer more than its competing 5'-atifitial-mismatch primers, as in Examples 2-4.

Example 1

Materials and Methods
Preparation of Primers
3' ddCMP blocked primers were chemically synthesized in 3'-5' direction and purified by HPLC by Integrated DNA Technologies.

3' ddAMP, ddTMP and ddGMP blocked primers were synthesized enzymatically by adding ddATP, ddTTP and ddGTP to the 3' ends of oligodeoxynucleotides by terminal transferase (Liu and Sommer, 2000; Liu and Sommer, 2002). Then they were purified by 7M urea/16% polyacrylamide gel electrophoresis. The amount of each recovered primer was determined by UV absorbance at 260 nm.
Preparation of Templates
Genomic DNA was extracted from blood white cells using QIAamp Blood Mini Kit according to Qiagen's protocol. Recombinant plasmid DNA was constructed by inserting into pUC57 vector a 100-400 bp target DNA segment which was chemically synthesized or PCR amplified. After transformed into E. coli, the recombinant plasmid DNA was extracted using QIAamp Plasmid Mini Kit according to Qiagen's protocol. The eluted DNA was dissolved in TE buffer (10 mM Tris-HCl, 0.1 mM EDTA, pH8.0) and its amount was determined by UV absorbance at 260 nm.
PAP Reaction
Unless stated otherwise, the PAP reaction mixture of 20 μl contained 88 mM Tris-HCl (pH 8.0 at 25° C.), 10 mM $(NH_4)_2SO_4$, 1.2-2.5 mM $MgCl_2$, 25 μM each dNTPs (dATP, dTTP, dGTP and dCTP), 0.1 μM each primers, 90 μM $Na_4PP_i$, 0.1× SybrGreen I dye, 1-2 units of polymerase, and starting DNA template.
Thermocycling
A Bio-Rad CFX96 real-time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

A cycling entailed 96° C. for 12 seconds, 60° C. for 30 seconds, 64° C. for 30 seconds, and 68° C. for 30 seconds for a total of 40 cycles; or another cycling entailed 96° C. for 12 seconds, 64° C. for 45 seconds, and 68° C. for 45 seconds for a total of 40 cycles. A denaturing step of 96° C. for 2 min was added before the first cycle.

To confirm the amplified product, melting curving analysis was followed from 68° C. to 95° C. with increment 0.5° C. and holding 5 seconds to confirm the specific amplified product.
Serial Dilution Experiment to Determine Amplification Efficiency
In order to determine the amplification efficiency, the template of plasmid or genomic DNA was 10-fold serially diluted from $10^6$ to 10 copies per 20 ul of reaction. In real-time PAP, Ct value was measured for each reaction which is proportional to the amount of amplified product in the early exponential phase of amplification. In addition, melting temperature was measured to confirm the specific amplified product.

Then Ct values are plotted with log DNA copies so that the equation of linear regression, coefficient of determination ($R^2$), and slop can be calculated. The slope is converted into the amplification efficiency by a formula: Efficiency= $10^{(-1/slope)}-1$.

Example 2

One-Locus-Duplex-PAP in Exon 19 of the EGFR Gene
In a One-Locus-Duplex-PAP, two pairs of 5'-artificial-mismatch blocked primers COSM6255 and COSM12369 (SEQ ID 15 and 16, 19 and 16) were developed to detect two deletions of del2239_2256, an 18 base deletion COSM6255 (SEQ ID 13), and del2240_2254, a 15 base deletion COSM12369 (SEQ ID 17) in exon 19 of the EGFR gene (Table 2).

For the forward primer (SEQ ID 15) of the first pair COSM6255, two artificial mutations were introduced into the 5' region, i.e., a T to G at the $4^{th}$ nucleotide and an A to C at the $7^{th}$ nucleotide from the 5' end. The 3' end has two nucleotides, CddC, that are specific to the templates COSM6255 (SEQ ID 13 and 14), but mismatch the wildtype and other templates, providing high discrimination. For the reverse primer (SEQ ID 16) of the first pair, it is shared by the second pair of primers and no artificial mutations were introduced (Table 2).

For the forward primer (SEQ ID 19) of the second pair COSM12369, two artificial mutations were introduced into the 5' region, i.e., a T to G at $3^{rd}$ nucleotide, an A to C at $6^{th}$ nucleotide from the 5' end. The 3' end has two nucleotides, CddT, that are specific to the templates COSM12369 (SEQ ID 17 and 18), but mismatch the wildtype and other templates (Table 2).

FIG. 1 shows how the 5'-artificial-mismatch primers work with the two pairs of primers COSM6255 and COSM12369 (SEQ ID No 15 and 16, 19 and 16). Only the 5' regions of primers (SQE ID 15 and 19) are diagramed with the complementary strands of the starting and duplicated templates COSM6255 (SEQ ID 13 and 14). The number of mismatches varies from zero to 4, depending on combination of the specific primer and template, indicating the mechanism how to reduce the inhibitory interaction among the primers.

Table 3 describes a more complex situation. Rather than amplify one template in FIG. 1, the two pairs of primers COSM6255 and COSM12369 (SEQ ID No 15 and 16, 19 and 16) amplify the templates COM625 and COSM 12369 (SEQ NO 13 and 14, 17 and 18) in one reaction. Only the 5' regions of the forward 5'-artificial-mismatch primers (SEQ ID 15 and 19) are counted with the complementary strands of the starting and duplicated templates COM625 and COSM 12369 (SEQ NO 13 and 14, 17 and 18). The number and type of mismatches between the 5' regions and the complementary strands of the templates are shown, indicating again the mechanism: 1) a 5'-atifitial-mismatch primer matches its corresponding templates more than its competing templates in the 5' region, and 2) a template matches its corresponding 5'-atifitial-mismatch primer more than its competing 5'-atifitial-mismatch primers in the 5' region.

The One-Locus-Duplex-PAP used the two pairs of primers COSM6255 and COSM12369 (SEQ ID No 15 and 16, 19 and 16) to amplify the potential templates COSM6255 and COSM12369 (SEQ ID 13 and 14, 17 and 18), individually or together (FIG. 2, Table 2). For comparison, the Singleplex-PAP used a pair of primers to amplify its corresponding templates.

To determine the amplification efficiencies, the starting templates were 10-fold serially diluted from $10^6$ to 10 copies per 20 ul of reaction (FIG. 2, Table 2). No inhibitory interaction was observed because the efficiency difference between the Singleplex-PAP and One-locus-Duplex-PAP is <5% to amplify the same template.

Example 3

One-Locus-Triplex-PAP in Exon 18 of the EGFR Gene

In a One-Locus-Triplex-PAP, three pairs of 5'-artificial-mismatch blocked primers COSM6252, COSM6253 and COSM6239 (SEQ ID 22 and 23, 26 and 27, 30 and 31) were developed in exon 18 of the EGFR gene (Table 4).

For each primer, an artificial mutation was introduced into the 5' region (Table 4). For example, for the forward primer (SEQ ID 22) of the first pair COSM6252, an A to C artificial mutation was introduced at the $5^{th}$ nucleotide from the 5' end. For the forward primer (SEQ ID 26) of the second pair COSM6253, a T to G was introduced at $7^{th}$ nucleotide from the 5' end. For the forward primer (SEQ ID 30) of the third pair COSM6239, a T to G was introduced at $7^{th}$ nucleotide from the 5' end.

FIG. 3 and Table 5 show how the 5'-artificial-mismatch primers work with the three pairs of primers COSM6252, COSM6253 and COSM6239 (SEQ ID 22 and 23, 26 and 27, 30 and 31). Only the 5' regions of the forward primers (SEQ ID 22, 26 and 30) are counted with the complementary strands of the corresponding starting and duplicated templates. The number of mismatches between the 5' regions and the complementary strands of the templates varies from zero to 2, depending on combination of the specific primer and template, indicating the mechanism.

In addition, for the first pair of primers COSM6252 (SEQ ID 22 and 23), the 3' ends are specific to the templates COSM6252 (SEQ ID 20 and 21) that contain c.2155G>A substitution in exon 18 of the EGFR gene, but mismatch the wildtype and other templates, providing high discrimination. For the second pair of primers COSM6253 (SEQ ID 26 and 27), the 3' ends are specific to the templates COSM6253 (SEQ ID 24 and 25) that contain c.2155G>T substitution, but mismatch the wildtype and other templates. For the third pair of primers COSM6239 (SEQ ID 30 and 31), the 3' ends are specific to the templates COSM6239 (SEQ ID 28 and 29) that contain c.2156G>C substitution, but mismatch the wildtype and other templates.

The One-Locus-Triplex-PAP used the three pairs of primers COSM6252, COSM6253 and COSM6239 (SEQ ID 22 and 23, 26 and 27, 30 and 31) to amplify the potential templates COSM6252 (SEQ ID 20 and 21), COSM6253 (SEQ ID 24 and 25) and COSM6239 (SEQ ID 28 and 29), individually or together (FIG. 4, Table 4). For comparison, the Singleplex-PAP used a pair of primers to amplify its corresponding template.

Through 10-fold serial dilution of the starting templates, amplification efficiencies of the Singleplex-PAP and One-Locus-Duplex-PAP were determined (FIG. 4, Table 4). No inhibitory interaction was observed by using 5'-artificial-mismach primers in the One-Locus-Triplex-PAP in exon 18 of the EGFR gene.

Example 4

One-Locus-Triplex-PAP in Exon 2 of the KRAS Gene

In a One-Locus-Triplex-PAP, three pairs of 5'-artificial-mismatch blocked primers COSM518, COSM516 and COSM517 (SEQ ID 34 and 35, 38 and 39, 42 and 43) were developed in exon 2 of the KRAS gene (Table 6).

For each primer, an artificial mutation was introduced into the 5' region (Table 6). For example, for the forward primer (SEQ ID 34) of the first pair COSM518, an A to C artificial mutation was introduced at the $5^{th}$ nucleotide from the 5' end. For the forward primer (SEQ ID 38) of the second pair COSM516, an A to C was introduced at $7^{th}$ nucleotide from the 5' end. For the forward primer (SEQ ID 42) of the third pair COSM517, an A to C was introduced at $9^{th}$ nucleotide from the 5' end.

FIG. 5 and Table 7 show how the 5'-artificial-mismatch primers work with the three pairs of the primers COSM518, COSM516 and COSM517 (SEQ ID 34 and 35, 38 and 39, 42 and 43). Only the 5' regions of the forward primers (SEQ ID 34, 38 and 42) are considered with the complementary strands of the corresponding starting and duplicated templates. The number of mismatches between the 5' regions and the complementary strands of the templates varies from zero to 2, depending on combination of the specific primer and template, indicating the mechanism.

For the first pair of primers COSM518 (SEQ ID 34 and 35), the 3' ends are specific to the templates COSM518 (SEQ ID 32 and 33) that contain c.34G>C substitution in exon 2 of the KRAS gene, but mismatch the wildtype and other templates, providing the high discrimination. For the second pair of primers COSM516 (SEQ ID 38 and 39), the 3' ends are specific to the templates COSM516 (SEQ ID 36 and 37) that contain c.34G>T substitution, but mismatch the wildtype and other templates. For the third pair of primers COSM517 (SEQ ID 42 and 43), the 3' ends are specific to the templates COSM517 (SEQ ID 40 and 41) that contain c.34G>A substitution, but mismatch the wildtype and other templates.

The One-Locus-Triplex-PAP used the three pairs of primers COSM518, COSM516 and COSM517 (SEQ ID 34 and 35, 38 and 39, 42 and 43) to amplify the potential templates COSM518 (SEQ ID 32 and 33), COSM516 (SEQ ID 36 and 37) and COSM517 (SEQ ID 40 and 41), individually or together (FIG. 6, Table 6). For comparison, the Singleplex-PAP used a pair of primers to amplify its corresponding template.

Through 10-fold serial dilution of the starting templates, amplification efficiencies of the Singleplex-PAP and One-Locus-Duplex-PAP were determined (FIG. 6, Table 6). No inhibitory interaction was observed by using 5'-artificial-mismach primers in the One-Locus-Triplex-PAP in exon 2 of the KRAS gene.

Example 5

Multiplex PAP and Parallel Sequencing of Individual Molecules of the Amplified Products A Multiplex PAP System was developed to amplify multiple potential cancer-specific somatic mutations in the KRAS, EGFR, NRAS and BRAF genes in non-small cell lung cancer (NSCLC) in a single reaction.

Specifically, a total of 33 pairs of blocked primers were used in a reaction to amplify 40 potential mutant templates, including those of One-Locus-Multiplex-PAP to amplify almost-sequence-identical mutant templates in the same locus in which at least a blocked primer of a pair has one or two artificial mutations introduced into its 5' region (Table 8).

Typically, only a few of such potential mutants that are actually present in the sample can be amplified in the reaction. To identify and differentiate the amplified products, individual molecules were sequenced in parallel with their frequencies scored.

One-Locus-Multiplex-PAP to Amplify Multiple Templates Including Almost-Sequence-Identical Templates in a Single Reaction In order for this Multiplex PAP System to amplify not only efficiently but also evenly the multiple potential almost-sequence-identical templates, One-Locus-Multiplex-PAP was developed.

For the design, the multiple potential almost-sequence-identical templates, which are located at one locus in a genome and have at least one nucleotide variance from each other, are amplified by the multiple pairs of blocked primers. A least a primer of a pair has one or two artificial mutations introduced into its 5' region. In addition, the artificial mutations in the 5' regions of the multiple pairs of primers are located at different nucleotides at the locus of the genome.

KRAS Mutations

This Multiplex PAP System includes a component of One-Locus-Multiplex-PAP in the KRAS gene. Seven pairs of blocked primers were developed for seven mutations in exon 2 (Table 8, Table 9 and B).

EGFR Mutations

This Multiplex PAP System includes three components of One-Locus-Multiplex-PAP and Regular-Multiplex-PAP in the EGFR gene. Twelve pairs of blocked primers were developed for eighteen mutations (Table 8, Table 10 A and B).

A first component of Regular-Multiplex-PAP has three pair of blocked primer for three mutations scattered in exons 20 and 21, in which each primer of a pair has no artificial mutation introduced into its 5' region. A second component of One-Locus-Multiplex-PAP has three pairs of blocked primers for three G719X mutations in exon 18. A third component of One-Locus-Multiplex-PAP has six pairs of blocked primers for twelve deletions in exon 19.

NRAS Mutations

This Multiplex PAP System assay includes two components of One-Locus-Multiplex-PAP in the NRAS gene. Thirteen pairs of blocked primers were developed for thirteen mutations (Table 8, Table 11 A and B).

A first component of One-Locus-Multiplex-PAP has seven pairs of blocked primers for seven mutations in exon 2. A second component of One-Locus-Multiplex-PAP has six pairs of blocked primers for six mutations in exon 3.

BRAF Mutations

This Multiplex PAP System includes a component of PAP. One pair of blocked primers was a developed for two mutations in the BRAF gene (Table 8, Table 12A and B).

Multiplex PAP Amplification

The Multiplexed PAP System used all the above 33 pairs of blocked primers (each at 0.05 μM), including those for One-Locus-Multiplex-PAP, to amplify 40 potential templates in a reaction.

To simulate conditions in cancer genome, four recombinant plasmid DNA templates (each with 1000 copies) of EGFR C2369T (T790M, COSM 6240), EGFR T2573G (L858R, COSM 6224), EGFR Del2235_2249 (delE746-A750, COSM 6223) and KRAS G34C (G12R, COSM518) mutations were added for this amplification. After performing the thermocycling procedure for 30 cycles, the amplified products were collected for parallel sequencing.

Parallel Sequencing of Individual Molecules of the Amplified Products

Previously, a real time PCR machine needs two fluorescence signals to identify and differentiate two amplified products, greatly limiting the number of the multiple amplified products.

To resolve this problem, parallel sequencing was used to sequence individual molecules to identify and differentiate the multiple amplified products. Illumina next generation sequencer was exampled, and others like Thermo Fisher Ion Torrent, Oxford Nanopore and Pacific Biosciences SMRT sequencers can also be used. Through procedure of library preparation, cluster amplification, sequencing, and alignment and data analysis, individual molecules of the above four multiple amplified products were sequenced in parallel by an Illumina HiSeq Series sequencer.

Qualified reads originated from individual molecules were called with their numbers counted (Table 13). With high frequencies, most of the reads were aligned to either target of EGFR C2369T (T790M, COSM 6240), EGFR T2573G (L858R, COSM 6224), EGFR Del2235_2249 (delE746-A750, COSM 6223) and KRAS G34C (G12R, COSM518) mutations. Thus, the four amplified products were identified and differentiated, demonstrating the feasibility of sequencing individual molecules of the multiple amplified products in parallel. With low frequencies, the remaining reads could not be aligned to the four targets or any other human genome, constituting a background of unknown origin (Table 13).

The method of parallel sequencing has two advantages: 1) unlimited capacity to differentiate a large number of amplified products, and 2) additional resolution to recognize false amplified products.

Thus, we combine mmultiplex PAP amplification with parallel sequencing for ultrahigh-sensitive, ultrahigh-selective and ultrahigh-throughput detection of early cancer

REFERENCE

Aboul-ela F, Koh D, Tinoco I, Jr., Martin F H. 1985. Base-base mismatches. Thermodynamics of double helix formation for dCA3XA3G+dCT3YT3G (X, Y=A, C, G, T). Nucleic Acids Res 13(13):4811-24.

Deutscher M P, Kornberg A. 1969. Enzymatic synthesis of deoxyribonucleic acid. 28. The pyrophosphate exchange and pyrophosphorolysis reactions of deoxyribonucleic acid polymerase. J Biol Chem 244(11):3019-28.

Ikuta S, Takagi K, Wallace R B, Itakura K. 1987. Dissociation kinetics of 19 base paired oligonucleotide-DNA duplexes containing different single mismatched base pairs. Nucleic Acids Res 15(2):797-811.

Liu Q, Nguyen V Q, Li X, Sommer S S. 2006. Multiplex dosage pyrophosphorolysis-activated polymerization: application to the detection of heterozygous deletions. Biotechniques 40(5):661-8.

Liu Q, Sommer SS. 2000. Pyrophosphorolysis-activated polymerization (PAP): application to allele-specific amplification. Biotechniques 29(5):1072-1080.

Liu Q, Sommer SS. 2002. Pyrophosphorolysis-activatable oligonucleotides may facilitate detection of rare alleles, mutation scanning and analysis of chromatin structures. Nucleic Acids Res 30(2):598-604.

Liu Q, Sommer SS. 2004a. Detection of extremely rare alleles by bidirectional pyrophosphorolysis-activated polymerization allele-specific amplification (Bi-PAP-A): measurement of mutation load in mammalian tissues. Biotechniques 36(1):156-66.

Liu Q, Sommer SS. 2004b. PAP: detection of ultra rare mutations depends on P* oligonucleotides: "sleeping beauties" awakened by the kiss of pyrophosphorolysis. Hum Mutat 23(5):426-36.

Liu Q, Sommer SS. 2004c. Pyrophosphorolysis by Type II DNA polymerases: implications for pyrophosphorolysis-activated polymerization. Anal Biochem 324(1):22-8.

Modrich P. 1987. DNA mismatch correction. Annu Rev Biochem 56:435-66.

Piao X, Sun L, Zhang T, Gan Y, Guan Y. 2008. Effects of mismatches and insertions on discrimination accuracy of nucleic acid probes. Acta Biochim Pol 55(4):713-20.

TABLE 1

Inhibition in One-Locus-Duplex-PAP using 5'-perfect-match primers

| # | Locus[a] | Chromosome[a] | Bi-allelic template and primer | Sequence (5' to 3') (SEQ ID NO) |
|---|---|---|---|---|
| 1 | Rs4261 | 7q | A allele A-allelic template[b] | 5'ggctaaaattatccctgggctctcagtaaAgccaatt gatgtcatcacttggacagtgt3' (1) |
| | | | A-Forward primer[c] | 5'GGCTAAAATTATCCCTGGGCTCTCAGTAAddA (2) |
| | | | A-Reverse primer | 5'ACACTGTCCAAGTGATGACATCAATTGGCddT (3) |
| | | | T allele T-allelic template | 5'ggctaaaattatccctgggctctcagtaaTgccaatt gatgtcatcacttggacagtgt3' (4) |
| | | | T-Forward primer | 5'GGCTAAAATTATCCCTGGGCTCTCAGTAAddT (5) |
| | | | T-Reverse primer | 5'ACACTGTCCAAGTGATGACATCAATTGGCddA (6) |
| 2 | Rs31224 | 5q | A allele A-allelic template | 5'ctgctcactgctaatggggttatgcggttAcaaggg cgtgcatcatttcgcacacccag3' (7) |
| | | | Forward primer | 5'CTGCTCACTGCTAATGGGGTTATGCGGTTddA (8) |
| | | | Reverse primer | 5'CTGGGTGTGCGAAATGATGCACGCCCTTGddT (9) |
| | | | T allele T-allelic template | 5'ctgctcactgctaatggggttatgcggttTcaaggg cgtgcatcatttcgcacacccag3' (10) |
| | | | Forward primer | 5'CTGCTCACTGCTAATGGGGTTATGCGGTTddT (11) |
| | | | Reverse primer | 5'CTGGGTGTGCGAAATGATGCACGCCCTTGddA (12) |

Footnotes of Table 1.
[a]From www.ncbi.nlm.nih.gov/snp/, Rs4261 is a A/T biallelic polymorphism and Rs31224 is another A/T biallelic polymorphism.
[b]The downstream strand is shown for the template Rs4261. The upper and bold case is the biallelic nucleotide.
[c]ddA, underlined, is a dideoxynucleotide located at the 3' end as a blocker. It matches the A allele-specific template Rs4261, but mismatched to the T allele-specific-template Rs4261 at the 3' end.

TABLE 2

5'-artificial-mismatch primers for One-Locus-Duplex-PAP in exon 19 of the EGFR gene

| # | COSMIC ID[ab] | Target[b] | Template and primer | Sequence (5' to 3') (SEQ ID NO) | Artificial mutation[f] Type | nt from the 5' end |
|---|---|---|---|---|---|---|
| 1 | COSM6255 | del2239_2256 | Starting Template[c] | 5'agttaaaattcccgtcgctatcaaggaaccgaa agccaacaaggaaatcctcgatgtgagtttc3' (13) | | |
| | | | Duplicated template[c] | 5'agtGaaCattcccgtcgctatcaaggaaccg aaagccaacaaggaaatcctcgatgtgagtttc3, (14) | | |
| | | | Forward primer[d] | 5'AGTGAACATTCCCGTCGCTA TCAAGGAACddC (15) | T to G, A to C | 4, 7 |
| | | | Reverse primer[e] | 5'GAAACTCACATCGAGGATTT CCTTGTTGGddC (16) | | |
| 2 | COSM12369 | del2240-2254 | Starting Template | 5'agttaaaattcccgtcgctatcaaggaatctcc gaaagccaacaaggaaatcctcgatgtgagtttc 3'(17) | | |
| | | | Duplicated template | 5'agGtaCaattcccgtcgctatcaaggaatct ccgaaagccaacaaggaaatcctcgatgtgagt ttc3' (18) | | |

TABLE 2-continued

5'-artificial-mismatch primers for One-Locus-Duplex-PAP in exon 19 of the EGFR gene

| | Forward primer | 5'AGGTACAATTCCCGTCGCTATCAAGGAAT<u>CddT</u> (19) | T to G, A to C | 3, 6 |
|---|---|---|---|---|
| | Reverse primer[e] | 5'GAAACTCACATCGAGGATTTCCTTGTTGG<u>ddC</u> (16) | | |

| # | COSMIC ID[a,b] | Target[b] | Template and primer | Amplification efficiency | | Inhibition in Duplex-PAP[i] |
|---|---|---|---|---|---|---|
| | | | | Singleplex-PAP[g] | Duplex-PAP[h] | |
| 1 | COSM6255 | del2239_2256 | Starting Template[c] Duplicated template[c] Forward primer[d] Reverse primer[e] | 99.4% | 99.6% | 0.2%[i], No |
| 2 | COSM12369 | del2240-2254 | Starting Template Duplicated template Forward primer Reverse primer[e] | 96.7% | 95.2% | 1.5%, No |

Footnotes of Table 2.
[a]From www.sanger.ac.uk/genetics/CGP/cosmic/
[b]COSM6255 contains del2239_2256 deletion, and COSM 12369 contains del2240_2254 deletion in exon 19 of the EGFR gene.
[c]Only the downstream strand of the template is shown. For the duplicated template, the two upper, bold and underlined cases are corresponding artificial mutations duplicated from the 5'-artificial-mismatch primer, and can be taken as template in later cycles.
[d]Forward primer is a 5'-artificial-mismatch primer in which two artificial mutations G and C are indicated as bold and underlined cases. In addition, the underlined <u>CddC</u> are two nucleotides at the 3' end that are specific to COSM6255 template, but mismatch the wildtype sequence.
[e]Reverse primer is used for both pairs of primers, and no artificial mutations are introduced for this primer.
[f]Artificial mutation is indicated with the type and location from the 5' end of a primer.
[g]In the Singleplex-PAP, the first pair of primers amplified the first template in a first reaction, and the second pair of primers amplified the second template in a second reaction to determine their amplification efficiencies.
[h]In the One-Locus-Duplex-PAP, the two pairs of primers amplified the first template in a first reaction and the second template in a second reaction, respectively.
[i]Inhibition is called Yes if the efficiency difference between the Singleplex-PAP and One-locus-Duplex-PAP is ≥5% to amplify the same template, or No if it is <5%. 0.2% is the efficiency difference between the Singleplex-PAP and One-locus-Duplex-PAP.

TABLE 3

The number and type of mismatches between the 5' regions of 5'-artificial-mismatch primers and the templates in exon 19 of the EGFR gene by One-Locus-Duplex-PAP

| | | | Artificial mutation in the 5' region of the forward primer[a] | |
|---|---|---|---|---|
| | | | COSM6255 T to G at 4$^{th}$ nt, A to C at 7$^{th}$ nt[b] | COSM12369 T to G at 3$^{rd}$ nt, A to C at 6$^{th}$ nt |
| # | | Complementary strand of the template | | |
| 1 | COSM 6255 | Starting[a] | 2, G-A, C-T[c] | 2, G-A, C-T |
| | | Duplicated[a] | 0 | 4, G-A, T-C, C-T, A-G |
| 2 | COSM 12369 | Starting | 2, G-A, C-T | 2, G-A, C-T |
| | | Duplicated | 4, T-C, G-A, A-G, C-T | 0 |

Footnotes of Table 3.
[a]Only the 5' regions of the forward 5'-artificial-mismatch primers and the complementary strands of the starting and duplicated templates are considered in the One-Locus-Duplex-PAP.
[b]T to G at 4$^{th}$ nt, A to C at 7$^{th}$ nt means that two artificial mutations of a T to G artificial mutation at the 4$^{th}$ nucleotide from the 5' end, and an A to C artificial mutation at the 7$^{th}$ nucleotide from the 5' end are contained in the 5' region of the forward 5'-artificial-mismatch primer COSM6255.
[c]2 means two artificial mismatches. For example, a G-A mismatch is formed between the 5' region of the forward 5'-artificial-mismatch primer COSM6255 and the complementary strand of the starting template COSM6255. The artificial mismatch is the 4$^{th}$ nucleotide calculated from the 5' end of the primer.

TABLE 4

5'-artificial-mismatch primers for One-Locus-Triplex-PAP
in exon 18 of the EGFR gene

| # | COSMIC ID[a] | Target[a] | Template and primer | Sequence (5' to 3') (SEQ ID NO) | 5' artificial mismatch Type | nt from 5'end |
|---|---|---|---|---|---|---|
| 1 | COSM6252 | c.2155G > A | Starting Template | 5'actgaattcaaaaagatcaaagtgctgAgctc cggtgcgttcggcacggtgtata3' (20) | | |
| | | | Duplicated template | 5'actgCattcaaaaagatcaaagtgctgAgct ccggtgcgttcggcacTgtgtata3' (21) | | |
| | | | Forward Primer | 5'ACTGCATTCAAAAAGATCA AAGTGCTGddA (22) | A to C | 5 |
| | | | Reverse primer | 5'TATACACAGTGCCGAACGC ACCGGAGCddT (23) | C to A | 8 |
| 2 | COSM6253 | c.2155G > T | Starting Template | 5'actgaattcaaaaagatcaaagtgctgTgctc cggtgcgttcggcacggtgtata3' (24) | | |
| | | | Duplicated template | 5'actgaaGtcaaaaagatcaaagtgctgTgct ccggtgcgttcggcaAggtgtata3' (25) | | |
| | | | Forward Primer | 5'ACTGAAGTCAAAAAGATCA AAGTGCTGddT (26) | T to G | 7 |
| | | | Reverse primer | 5'TATACACCTTGCCGAACGCA CCGGAGCddA (27) | G to T | 9 |
| 3 | COSM6239 | c.2156G > C | Starting Template | 5'ctgaattcaaaaagatcaaagtgctggCctcc ggtgcgttcggcacggtgtataa3' (28) | | |
| | | | Duplicated template | 5'ctgaatGcaaaaagatcaaagtgctggCct ccggtgcgttcggcacgAtgtataa3' (29) | | |
| | | | Forward Primer | 5'CTGAATGCAAAAAGATCAA AGTGCTGGddC (30) | T to G | 7 |
| | | | Reverse primer | 5'TTATACAACGTGCCGAACGC ACCGGAGddG (31) | C to A | 8 |

| # | COSMIC ID[a] | Target[a] | Template and primer | Amplification efficiency | | Inhibition in Triplex-PAP |
|---|---|---|---|---|---|---|
| | | | | Singleplex-PAP[b] | Triplex-PAP[c] | |
| 1 | COSM6252 | c.2155G > A | Starting Template Duplicated template Forward Primer Reverse primer | 99.9% | 101.3% | 0.4%, No |
| 2 | COSM6253 | c.2155G > T | Starting Template Duplicated template Forward Primer Reverse primer | 98.1% | 95.6% | 2.5%, No |
| 3 | COSM6239 | c.2156G > C | Starting Template Duplicated template Forward Primer Reverse primer | 97.3% | 97.0% | 0.3%, No |

Footnotes of Table 4.
[a]COSM6252 contains c.2155G > A substitution, COSM6253 contains c.2155G > T substitution, and COSM6239 contains c.2156G > C substitution in exon 18 of the EGFR gene. The three substitutions are located at two neighboring nucleotides in the sequences.
[b]In the Singleplex-PAP, the first pair of primers amplified the first template in a first reaction, the second pair of primers amplified the second template in a second reaction, and the third pair of primers amplified the third template in a third reaction to determine their amplification efficiencies.
[c]In the One-Locus-Triplex-PAP, the three pairs of primers amplified the first template in a first reaction, the second template in a second reaction, and the third template in a third reaction, respectively.

TABLE 5

The number and type of mismatches between the 5' regions of 5'-artificial-mismatch primers and the templates in exon 18 of the EGFR gene by One-Locus-Triplex-PAP[a]

| # | Complementary strand of the template | | COSM6252 A to C at 5th nt | COSM6253 T to G at 7th nt[b] | COSM6239 T to G at 7th nt[b] |
|---|---|---|---|---|---|
| 1 | COSM6252 | Starting | 1, C-T | 1, G-A | 1, G-A |
|   |          | Duplicated | 0 | 2, A-G, G-A | 2, A-G, G-A |
| 2 | COSM6253 | Starting | 1, C-T | 1, G-A | 1, G-A |
|   |          | Duplicated | 2, C-T, T-C | 0 | 2, T-C, G-A |
| 3 | COSM6239 | Starting | 1, C-T | 1, G-A | 1, G-A |
|   |          | Duplicated | 2, C-T, T-C | 2, G-A, T-C | 0 |

Footnotes of Table 5.
[a] The One-Locus-Triplex-PAP used the three pairs of primers COSM6252, COSM6253 and COSM6239 (SEQ ID 22 and 23, 26 and 27, 30 and 31) to amplify the templates COSM6252 (SEQ ID 20 and 21), COSM6253 (SEQ ID 24 and 25) and COSM6239 (SEQ ID 28 and 29) in a reaction.
[b] Although the two artificial mutations of the two forward primers are at the same location calculated from their 5' ends, they are located at different nucleotides in the templates.

TABLE 6

5'-artificial-mismatch primers for One-Locus-Triplex-PAP in exon 2 of the KRAS gene

| COSMIC # ID[a] | Target[a] | Template and primer | Sequence (5' to 3') (SEQ ID NO) | 5' artificial mismatch Type | nt from 5' end |
|---|---|---|---|---|---|
| 1 COSM518 | c.34G > C | Starting Template | 5'ctgaatataaacttgtggtagttggagctCgtgg cgtaggcaagagtgccttgacgata3' (32) | | |
| | | Duplicated template | 5'ctgaCtataaacttgtggtagttggagctCgtg gcgtaggcaagagtgcAttgacgata3' (33) | | |
| | | Forward primer | 5'CTGACTATAAACTTGTGGTAG TTGGAGCTddC (34) | A to C | 5 |
| | | Reverse primer | 5'TATCGTCAATGCACTCTTGCC TACGCCACddG (35) | G to T | 10 |
| 2 COSM516 | c.34G > T | Starting Template | 5'ctgaatataaacttgtggtagttggagctTgtgg cgtaggcaagagtgccttgacgata3' (36) | | |
| | | Duplicated template | 5'ctgaatCtaaacttgtggtagttggagctTgtgg cgtaggcaagagtgccttTacgata3' (37) | | |
| | | Forward primer | 5'CTGAATCTAAACTTGTGGTAG TTGGAGCTddT (38) | A to C | 7 |
| | | Reverse primer | 5'TATCGTAAAGGCACTCTTGCC TACGCCACddA (39) | C to A | 7 |
| 3 COSM517 | c.34G > A | Starting Template | 5'ctgaatataaacttgtggtagttggagctAgtgg cgtaggcaagagtgccttgacgata3' (40) | | |
| | | Duplicated template | 5'ctgaatatCaacttgtggtagttggagctAgtg gcgtaggcaagagtgccttgTcgata3' (41) | | |
| | | Forward Primer | 5'CTGAATATCAACTTGTGGTAG TTGGAGCTddA (42) | A to C | 9 |
| | | Reverse primer | 5'TATCGACAAGGCACTCTTGCC TACGCCACddT (43) | T to A | 6 |

| COSMIC # ID[a] | Target[a] | Template and primer | Amplification efficiency Singleplex-PAP[b] | Amplification efficiency Triplex-PAP[c] | Inhibition in Triplex-PAP |
|---|---|---|---|---|---|
| 1 COSM518 | c.34G > C | Starting Template Duplicated template Forward primer Reverse primer | 98.8% | 97.8% | 1.0%, No |

TABLE 6-continued

5'-artificial-mismatch primers for One-Locus-Triplex-PAP in exon 2 of the KRAS gene

| | | | | | | |
|---|---|---|---|---|---|---|
| 2 | COSM516 | c.34G > T | Starting Template Duplicated template Forward primer Reverse primer | 97.5% | 98.9% | 1.4%, No |
| 3 | COSM517 | c.34G > A | Starting Template Duplicated template Forward Primer Reverse primer | 98.8% | 100.1% | 1.3%, No |

Footnotes of Table 6.
[a]COSM518 contains c.34G > C substitution, COSM516 contains c.34G > T substitution, COSM517 contains c.34G > A substitution in exon 2 of the KRAS gene. The three substitutions are located at two neighboring nucleotides in the sequences.
[b]In the Singleplex-PAP, the first pair of primers amplified the first template in a first reaction, the second pair of primers amplified the second template in a second reaction, and the third pair of primers amplified the third template in a third reaction to determine their amplification efficiencies.
[c]In the One-Locus-Triplex-PAP, the three pairs of primers amplified the first template in a first reaction, the second template in a second reaction, and the third template in a third reaction.

TABLE 7

The number and type of mismatches between the 5' regions of 5'-artificial-mismatch primers and the templates in exon 2 of the KRAS gene by One-Locus-Triplex-PAP[a]

| # | | Complementary strand of the template | Artificial mutation in the 5' region of the forward primer | | |
|---|---|---|---|---|---|
| | | | COSM518 A to C at 5th nt | COSM516 A to C at 7th nt | COSM517 A to C at 9th nt |
| 1 | COSM 518 | Starting | 1, C-T | 1, C-T | 1, C-T |
| | | Duplicated | 0 | 2, A-G, C-T | 2, A-G, C-T |
| 2 | COSM 516 | Starting | 1, C-T | 1, C-T | 1, C-T |
| | | Duplicated | 2, C-T, A-G | 0 | 2, A-G, C-T |
| 3 | COSM 517 | Starting | 1, C-T | 1, C-T | 1, C-T |
| | | Duplicated | 2, C-T, A-G | 2, C-T, A-G | 0 |

Footnotes of Table 7.
[a]The One-Locus-Triplex-PAP used the three pairs of primers COSM518, COSM516 and COSM517 (SEQ ID 34 and 35, 38 and 39, 42 and 43) to amplify the templates COSM518 (SEQ ID 32 and 33), COSM516 (SEQ ID 36 and 37) and COSM517 (SEQ ID 40 and 41) in a reaction.

TABLE 8

Summary of components in the Multiplex PAP System[a]

| Gene | Exon | Mutation type | Number of mutations | Number of pairs of primers | In one locus | Type of Multiplex-PAP |
|---|---|---|---|---|---|---|
| KRAS[b] | 2 | Single base | 7 | 7 | Yes | One-Locus- |
| EGFR | 20, 21 | Single base | 3 | 3 | No | Regular- |
| | 18 | Single base | 3 | 3 | Yes | One-Locus- |
| | 19 | Deletion | 12 | 6 | Yes | One-Locus- |
| NRAS | 2 | Single base | 7 | 7 | Yes | One-Locus- |
| | 3 | Single base | 6 | 6 | Yes | One-Locus- |
| BRAF | | Single base | 2 | 1 | No | Regular- |
| Total | | | 40 | 33 | | |

TABLE 8-continued

Summary of components in the Multiplex PAP System[a]

| Gene | Exon | Mutation type | Number of mutations | Number of pairs of primers | In one locus | Type of Multiplex-PAP |
|---|---|---|---|---|---|---|

Footnotes of Table 8
[a]The Multiplex PAP System contains components of One-Locus-Multiplex-PAP and Regular-Multiplex-PAP, depending on whether or not the individual assays are located at the same locus. For One-Locus-Multiplex-PAP, at least a blocked primer of a pair has one or two artificial mutations introduced into its 5' region (5' mutated primer), while for Regular-Multiplex-PAP, each primer of a pair has no artificial mutation introduced into its 5' region (5' perfect match primer).
[b]For example, the KRAS gene has seven mutations in the same locus within exon 2, and thus seven pairs of blocked primers are used for a component of One-Locus-Multiplex-PAP.

TABLE 9A

List of seven KRAS mutations

| #[a] | Exon | AA change | Mutation (CDS) | Relative frequency (%) | COSM ID |
|---|---|---|---|---|---|
| 1 | 2 | p.G12S | c.34G > A | 4.7 | COSM517 |
| 2 | 2 | p.G12R | c.34G > C | 3.3 | COSM518 |
| 3 | 2 | p.G12C | c.34G > T | 11.5 | COSM516 |
| 4 | 2 | p.G12D | c.35G > A | 34.8 | COSM521 |
| 5 | 2 | p.G12A | c.35G > C | 5.5 | COSM522 |
| 6 | 2 | p.G12V | c.35G > T | 23.7 | COSM520 |
| 7 | 2 | p.G13D | c.38G > A | 12.9 | COSM532 |
| Sum | | | | 96.3% | |

Footnotes of Table 9A
[a]The mutations in the KRAS gene are numbered from 1 to 7. The seven mutant templates are located at one locus of exon 2 and have at least one nucleotide variance from each other.

TABLE 9B

Seven pairs of blocked primers for the seven KRAS mutations

| #[a] | Primer | Sequence (5' to 3') (SEQ ID NO) | Type | 5' artificial mutation nt from 5' end |
|---|---|---|---|---|
| 1 | Forward primer | 5'CTGACTATAAACTTGTGGTAGTTGGAGCTdd<u>C</u> (42)[b] | A to C | 5 |
|   | Reverse primer | 5'TATCGTCAATGCACTCTTGCCTACGCCAdd<u>G</u> (43) | G to T | 10 |
| 2 | Forward primer | 5'CTGAATCTAAACTTGTGGTAGTTGGAGCTdd<u>T</u> (34) | A to C | 7 |
|   | Reverse primer | 5'TATCGTAAAGGCACTCTTGCCTACGCCAdd<u>A</u> (35) | C to A | 7 |
| 3 | Forward primer | 5'CTGAATATCAACTTGTGGTAGTTGGAGCTdd<u>A</u> (38) | A to C | 9 |
|   | Reverse primer | 5'TATCGACAAGGCACTCTTGCCTACGCCAdd<u>T</u> (39) | T to A | 6 |
| 4 | Forward primer | 5'TGAAGATAAACTTGTGGTAGTTGGAGCTGdd<u>A</u> (44) | T to G | 5 |
|   | Reverse primer | 5'GTATCGTCATGGCACTCTTGCCTACGCCAdd<u>T</u> (45) | A to T | 10 |
| 5 | Forward primer | 5'TGAATAGAAACTTGTGGTAGTTGGAGCTGdd<u>C</u> (46) | T to G | 7 |
|   | Reverse primer | 5'GTATCGACAAGGCACTCTTGCCTACGCCAdd<u>G</u> (47) | T to A | 7 |
| 6 | Forward primer | 5'TGAATATAGACTTGTGGTAGTTGGAGCTGdd<u>T</u> (48) | T to G | 9 |
|   | Reverse primer | 5'GTATAGTCAAGGCACTCTTGCCTACGCCAdd<u>A</u> (49) | C to A | 5 |
| 7 | Forward primer | 5'ATATAACCTTGTGGTAGTTGGAGCTGGTGdd<u>A</u> (50) | A to C | 7 |
|   | Reverse primer | 5'GCTGTAACGTCAAGGCACTCTTGCCTACGdd<u>T</u> (51) | T to A | 7 |

Footnotes of Table 9B
[a]The seven pairs of primers for the KRAS mutations are also numbered from 1 to 7. They are covered by a component of One-Locus-Multiplex-PAP in which a blocked primer of a pair has an artificial mutation introduced into its 5' region. In addition, the artificial mutations of the 5' mutated primers of the seven pairs are located at different nucleotides in exon 2 of the KRAS gene.
[b]The primer has an artificial mutation indicated as a bold and underlined case, and the type and location from the 5' end are also shown. In addition, the underlined ddC is a nucleotide at the 3' end that is specific to its template, but mismatches the wildtype sequence.

TABLE 10A

List of eighteen EGFR mutations

| #[a] | Exon | AA change | Mutation | Relative frequency (%) | COSM ID |
|---|---|---|---|---|---|
| 1 | 21 | L858R | T2573G | 40.1% | COSM 6224 |
| 2 | 21 | L861Q | T2582A | 1.6% | COSM 6213 |
| 3 | 20 | T790M | C2369T | 5.5% | COSM 6240 |
| 4 | 18 | G719A | G2156C | 1.0% | COSM 6239 |
| 5 | 18 | G719S | G2155A | 0.8% | COSM 6252 |
| 6 | 18 | G719C | G2155T | 0.6% | COSM 6253 |
| 7 | 19 | delE746-A750 | del2235_2249 del2236_2250 | 16.9% | COSM 6223 |
|   | 19 |   |   |   |   |
| 8 | 19 | delE746-S752insV | del2237_2255insT | 1.1% | COSM 12384 |
| 9 | 19 | delE746-S752insV | del2237_2256insTT | 0.1% | COSM 133194 |
| 10 | 19 | delE746-T751insVP | del2237_2253insTTCCT | 0.1% | COSM 52935 |
| 11 | 19 | delE746-A750 | del2236_2250 | 7.9% | COSM 6225 |
| 12 | 19 | del747-P753insS | del2240_2257 | 2.8% | COSM 12370 |

TABLE 10A-continued

List of eighteen EGFR mutations

| #[a] | Exon | AA change | Mutation | Relative frequency (%) | COSM ID |
|---|---|---|---|---|---|
| 13 | 19 | del747-P753insS | del2239_2257insT | 0.1% | COSM 133197 |
| 14 | 19 | delL747-A750insP | del2239_2248insC | 1.7% | COSM 12382 |
| 15 | 19 | delL747-S752 | del2239_2256 | 0.7% | COSM 6255 |
| 16 | 19 | delL747-A751insP | del2239_2251insC | 0.5% | COSM 12383 |
| 17 | 19 | delL747-T751 | del2240_2254 | 1.4% | COSM 12369 |
| 18 | 19 | delL747-T751 | del2238_2252 | 0.2% | COSM 23571 |
| Sum | | | | 82.8% | |

Footnotes of Table 10A
[a]The eighteen mutations in the EGFR gene are numbered from 1 to 18.

TABLE 10B

Twelve pairs of blocked primers for the eighteen EGFR mutations

| #[a] | Primer | Sequence (5' to 3') (SEQ ID NO) | 5' artificial mutation Type | nt from 5' end |
|---|---|---|---|---|
| 1 | Forward primer | 5'GCAGCATGTCAAGATCACAGATTTTGGGC<u>ddG</u> (52) | | |
| | Reverse primer | 5'CTTTCTCTTCCGCACCCAGCAGTTTGGCC<u>ddC</u> (53) | | |
| 2 | Forward primer | 5'CAAGATCACAGATTTTGGGCTGGCCAAAC<u>ddA</u> (54) | | |
| | Reverse primer | 5'CATGGTATTCTTTCTCTTCCGCACCCAGC<u>ddT</u> (55) | | |
| 3 | Forward primer | 5'CTGCCTCACCTCCACCGTGCAGCTCATCA<u>ddT</u> (56) | | |
| | Reverse primer | 5'CGGACATAGTCCAGGAGGCAGCCGAAG<u>ddG</u> (57) | | |
| 4 | Forward primer | 5'ACTGCATTCAAAAAGATCAAAGTGCTG<u>ddA</u> (22) | A to C | 5 |
| | Reverse primer | 5'TATACACAGTGCCGAACGCACCGGAGC<u>ddT</u> (23) | C to A | 8 |
| 5 | Forward primer | 5'ACTGAAGTCAAAAAGATCAAAGTGCTG<u>ddT</u> (26) | T to G | 7 |
| | Reverse primer | 5'TATACACCTTGCCGAACGCACCGGAGC<u>ddA</u> (27) | G to T | 9 |
| 6 | Forward primer | 5'CTGAATGCAAAAAGATCAAAGTGCTGG<u>ddC</u> (30) | T to G | 7 |
| | Reverse primer | 5'TTATACAACGTGCCGAACGCACCGGAG<u>ddG</u> (31) | C to A | 8 |
| 7 | Forward primer | 5'GAGACAGTTAAAATTCCCGTCGCTATCA<u>AAddC</u> (58) | A to C | 5 |
| 8-10 | Forward primer | 5'AAGTTAAAAGTCCCGTCGCTATCAAGG<u>TTddC</u> (59) | T to G | 10 |
| 11 | Forward primer | 5'GAAAGTTAAACTTCCCGTCGCTATCAAG<u>AddC</u> (60) | A to C | 11 |
| 12 | Forward primer | 5'AGTTAAAATGCCCGTCGCTATCAAGGAAT<u>CddG</u> (61) | T to G | 10 |
| 13-16 | Forward primer[b] | 5'AGTGAACATTCCCGTCGCTATCAAGGAA<u>CddC</u> (15) | T to G, A to C | 4, 7 |

TABLE 10B-continued

Twelve pairs of blocked primers for the eighteen EGFR mutations

| #[a] | Primer | Sequence (5' to 3') (SEQ ID NO) | 5' artificial mutation Type | nt from 5' end |
|---|---|---|---|---|
| 17-18 | Forward primer[b] | 5'AGGGTACAATTCCCGTCGCTATCAAGGAAT<u>Cdd</u><u>T</u> (19) | T to G, A to C | 3, 6 |
| 7-18 | Reverse prime[c] | 5'GAAACTCACATCGAGGATTTCCTTGTTGG<u>ddC</u> (16) | | |

Footnotes of Table 10B

[a]The twelve pairs of primers are numbered for the eighteen EGFR mutations. The 1st-3rd pairs are in a first component of Regular-Multiplex-PAP that each primer of a pair has no artificial mutations introduced into its 5' region. The 4th-6th pairs are in a second component of One-Locus-Multiplex-PAP. The 7th-18th pairs are in a third component of One-Locus-Multiplex-PAP.
[b]The forward primers has two artificial mutations introduced into its 5' region.
[c]In the third component of One-Locus-Multiplex-PAP, the reverse primer has no artificial mutations introduced into its 5' region and it pairs each of the six forward primers for deletions in exon 19.

TABLE 11A

List of thirteen NRAS mutations

| #[a] | Exon | AA change | Mutation (CDS) | Relative frequency (%) | COSM ID |
|---|---|---|---|---|---|
| 1 | 3 | p.Q61R | c.182A > G | 26.4 | COSM584 |
| 2 | 3 | p.Q61K | c.181C > A | 16.0 | COSM580 |
| 3 | 2 | p.G12D | c.35G > A | 15.4 | COSM564 |
| 4 | 2 | p.G13D | c.38G > A | 8.3 | COSM573 |
| 5 | 2 | p.G12S | c.34G > A | 4.3 | COSM563 |
| 6 | 3 | p.Q61L | c.182A > T | 4.5 | COSM583 |
| 7 | 2 | p.G13V | c.38G > T | 0.9 | COSM574 |
| 8 | 2 | p.G13R | c.37G > C | 4.1 | COSM569 |
| 9 | 3 | p.Q61H | c.183A > T | 2.7 | COSM585 |
| 10 | 2 | p.G12C | c.34G > T | 2.9 | COSM562 |
| 11 | 3 | p.Q61H | c.183A > C | 2.2 | COSM586 |
| 12 | 2 | p.G13C | c.37G > T | 0.9 | COSM570 |
| 13 | 3 | p.Q61P | c.182A > C | 0.7 | COSM582 |
| Sum | | | | 89.3% | |

Footnotes of Table 11A

[a]The thirteen mutations in the NRAS gene are numbered from 1 to 13.

TABLE 11B

Thirteen pairs of blocked primers for the thirteen NRAS mutations

| #[a] | Primer | Sequence (5' to 3') (SEQ ID NO) | 5' artificial mutation Type | nt from 5' end |
|---|---|---|---|---|
| 1 | Forward primer | 5'TTTGTTTGACATACTGGATACAGCTGGA<u>ddG</u> (62) | G to T | 7 |
|   | Reverse primer | 5'ATTGGTCACTCATGGCACTGTACTCTTCT<u>ddC</u> (63) | T to A | 8 |
| 2 | Forward primer | 5'GTTTGATGGACATACTGGATACAGCTGGA<u>ddA</u> (64) | T to A | 6 |
|   | Reverse primer | 5'TTGGTCTCACATGGCACTGTACTCTTCTT<u>ddT</u> (65) | T to A | 9 |
| 3 | Forward primer | 5'AGTACAAACAGGTGGTGGTTGGAGCAG<u>ddA</u> (66) | T to A | 10 |
|   | Reverse primer | 5'ATTGTCATTGCGCTTTTCCCAACACCA<u>ddT</u> (67) | G to T | 8 |
| 4 | Forward primer | 5'ACAAACTTGTGGTGGTTGGAGCAGGTG<u>ddA</u> (68) | G to T | 8 |
|   | Reverse primer | 5'CTGGATTGACAGTGCGCTTTTCCCAACA<u>ddT</u> (69) | T to A | 9 |
| 5 | Forward primer | 5'GAGTACACACTGGTGGTGGTTGGAGCA<u>ddA</u> (70) | A to C | 8 |
|   | Reverse primer | 5'TTGTCAGAGCGCTTTTCCCAACACCAC<u>ddT</u> (71) | T to A | 8 |

TABLE 11B-continued

Thirteen pairs of blocked primers for the thirteen NRAS mutations

| #[a] | Primer | Sequence (5' to 3') (SEQ ID NO) | 5' artificial mutation Type | nt from 5' end |
|---|---|---|---|---|
| 6 | Forward primer | 5'TTTGTAGGACATACTGGATACAGCTGGACddT (72) | T to A | 6 |
|   | Reverse primer | 5'ATTGGTCTATCATGGCACTGTACTCTTCTddA (73) | T to A | 9 |
| 7 | Forward primer | 5'ACAAACTGTTGGTGGTTGGAGCAGGTGddT (74) | G to T | 9 |
|   | Reverse primer | 5'TGGATGGTCAGTGCGCTTTTCCCAACAddA (75) | T to G | 6 |
| 8 | Forward primer | 5'TACAAAATGGTGGTGGTTGGAGCAGGTddC (76) | C to A | 7 |
|   | Reverse primer | 5'GGATTGTCCGTGCGCTTTTCCCAACACddG (77) | A to C | 9 |
| 9 | Forward primer | 5'TTGTTGGTCATACTGGATACAGCTGGACAddT (78) | A to T | 8 |
|   | Reverse primer | 5'TATTGGTATCTCATGGCACTGTACTCTTCddA (79) | C to A | 8 |
| 10 | Forward primer | 5'GAGTACAATCTGGTGGTGGTTGGAGCAddT (80) | A to T | 9 |
|   | Reverse primer | 5'TTGTAAGTGCGCTTTTCCCAACACCACddA (81) | C to A | 5 |
| 11 | Forward primer | 5'TTGTTGGAAATACTGGATACAGCTGGACAddC (82) | C to A | 9 |
|   | Reverse primer | 5'TATTGTTCTCTCATGGCACTGTACTCTTCddG (83) | G to T | 6 |
| 12 | Forward primer | 5'TACAAACTGGAGGTGGTTGGAGCAGGTddT (84) | T to A | 11 |
|   | Reverse primer | 5'GGATTTTCAGTGCGCTTTTCCCAACACddA (85) | G to T | 6 |
| 13 | Forward primer | 5'TTTGTTGTACATACTGGATACAGCTGGACddC (86) | G to T | 8 |
|   | Reverse primer | 5'ATTGGACTCTCATGGCACTGTACTCTTCTddG (87) | T to A | 6 |

Footnotes of Table 11B
[a]The thirteen pairs of primers for the thirteen NRAS mutations are also numbered from 1 to 18. They are covered by two components of One-Locus-Multiplex-PAP.

TABLE 12A

List of two BRAF mutations

| #[a] | AA change | Mutation (CDS) | Relative frequency (%) | COSM ID |
|---|---|---|---|---|
| 1 | V600E | c.1799T > A | 95 | COSM476 |
| 2 | V600K | c.1798_1799GT > AA | 2 | COSM473 |
| Sum | | | 97% | |

Footnotes of Table 12A
[a]The two mutations in the BRAF gene are numbered from 1 to 2.

TABLE 12B

One pair of blocked primers for the two BRAF mutations

| #[a] | Primer | Sequence (5' to 3') (SEQ ID NO) | 5' artificial mutation Type | nt from 5' end |
|---|---|---|---|---|
| 1, 2 | Forward primer | 5'CAGTAAAAATAGGTGATTTTGGTCTAGCTAddC (88) | | |
| | Reverse primer | 5'ACTGATGGGACCCACTCCATCGAGATTTCddT (89) | | |

Footnotes of Table 12B
[a]The pair of primers are used for the two BRAF mutations.

TABLE 13

List of mutations identified by sequencing

| # | Read aligned[a] | Number of reads observed | Relative frequency (%) | COSM ID |
|---|---|---|---|---|
| 1 | EGFR T790M | $6.3 \times 10^6$ | 29.3% | COSM 6240 |
| 2 | EGFR L858R | $4.5 \times 10^6$ | 20.7% | COSM 6224 |
| 3 | EGFR E19 deletion | $4.3 \times 10^6$ | 19.9% | COSM 6223 |
| 4 | KRAS G12R | $5.0 \times 10^6$ | 23.0% | COSM 518 |
| 5 | Not aligned to human genome | $1.6 \times 10^6$ | 7.2% | |
| Sum | | $21.6 \times 10^6$ | 100% | |

Footnotes of Table 13
[a]Read originates from individual molecules of the amplified products, and it is aligned to either template or complementary strand.

The invention claimed is:

1. A method for multiplex pyrophosphorolysis activated polymerization (PAP), comprising:

a) providing a plurality of pairs of forward and reverse blocked primers to amplify a plurality of potential templates in one reaction, wherein the blocked primers, with non-extendable, blocked nucleotides at their 3' ends, are activated by pyrophosphorolysis to produce a 3' unblocked primers and then extended by polymerization, which reactions are catalyzed by a polymerase, and wherein the templates are located at one locus consisting of 40 base pairs and have at least one nucleotide variance from each other, comprising:

i. a first pair of forward and reverse primers to amplify a first template, wherein the first forward primer or reverse primer has one or two one artificial mutations introduced into its 5' region forming one or two artificial mismatch between the 5' region and its template, and ii. a second pair of forward and reverse primers to amplify a second template which is located at the same locus as the first template but contains at least one nucleotide variance from the first template, wherein the second forward or reverse primer in the same direction as the above 5' mutated primer in the first pair has one or two one artificial mutations introduced into its 5' region forming one or two artificial mismatch between the 5' region and its template, wherein, the artificial mutations of the 5' mutated primers in the first pair and in the second pair are located at different nucleotides at the locus of the genome and have different mismatches between the two pairs of primers, each of which amplify a different template, and b) amplifying the templates in one reaction.

2. The method for multiplex PAP of claim 1, further comprising a step c) sequencing individual molecules of the multiple amplified products in parallel.

3. The method for multiplex PAP of claim 1, wherein the plurality of pairs of forward and reverse blocked primers further comprise a third pair of forward and reverse primers to amplify a third template which is located at the same locus as the first and second templates but contains at least one nucleotide variance from each of the first and second templates, wherein the third forward or reverse primer in the same direction as the above 5' mutated primer in the first and second pairs has at least one artificial mutation introduced into its 5' region, wherein, the artificial mutations of the 5' mutated primers in the first pair, the second pair and the third pair are located at different nucleotides at the locus of the genome.

4. The method for multiplex PAP of claim 1, wherein the plurality of pairs of forward and reverse blocked primers comprise:

i. the first pair of forward and reverse primers, wherein the other primer in the first pair comprises at least one artificial mutation in the 5' region in addition to the primer which already contains the artificial mutation, and ii. the second pair of forward and reverse primers, wherein the other primer in the second pair comprises at least one artificial mutation in the 5' region in addition to the primer which already contains the artificial mutation, wherein the artificial mutations of the 5' mutated primers in the first pair and the second pair are located at different nucleotides at the locus of the genome.

5. The method for multiplex PAP of claim 1, wherein the 3' regions of the first pair of primers match the first template but mismatch the second template, and the 3' regions of the second pair of primers match the second template but mismatch the first template, and wherein the first and second templates are located at the same locus but contain at least one nucleotide variance from each other.

6. The method for multiplex PAP of claim 1, wherein the artificial mutation of the 5' mutated primer in each of the first and second pairs is selected from the group consisting of six types of A to C, C to A, T to G, G to T, A to T, and T to A mutations.

7. The method for multiplex PAP of claim 1, wherein the artificial mutation of the 5' mutated primer in each of the first and second pairs result in one of the four types of mismatches of G-A, C-T, A-A, and T-T between the 5' region of the 5' mutated primer and the complementary strand of the template.

8. The method for multiplex PAP of claim 1, wherein the artificial mutation of the 5' mutated primer in any of the first and second pairs is selected from the group consisting of four types of A to C, C to A, T to G, and G to T mutations.

9. The method for multiplex PAP of claim 1, wherein the artificial mutation of the 5' mutated primer in any of the first and second pairs is selected from the group consisting of two types of A to T and T to A mutations.

10. The method for multiplex PAP of claim 1, wherein the 5' regions of the 5' mutated primers in the first and second pairs range from the first to the twelfth nucleotide from the 5' ends, including the nucleotides at the 5' ends assigned as the first nucleotides from the 5' ends.

11. The method for multiplex PAP of claim 1, wherein the first and second templates are completely or partially overlapped in the locus.

* * * * *

SEQUENCE LISTING

<160> NUMBER OF SEQ ID NOS: 89

<210> SEQ ID NO 1
<211> LENGTH: 59
<212> TYPE: DNA
<213> ORGANISM: Homo sapiens

<400> SEQUENCE: 1
ggctaaaatt atccctgggc tctcagtaaa gccaattgat gtcatcactt ggacagtgt        59

<210> SEQ ID NO 2
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 2
ggctaaaatt atccctgggc tctcagtaan                                        30

<210> SEQ ID NO 3
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 3
acactgtcca agtgatgaca tcaattggcn                                        30

<210> SEQ ID NO 4
<211> LENGTH: 59

```
<212> TYPE: DNA
<213> ORGANISM: Homo sapiens

<400> SEQUENCE: 4
ggctaaaatt atccctgggc tctcagtaat gccaattgat gtcatcactt ggacagtgt      59

<210> SEQ ID NO 5
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 5
ggctaaaatt atccctgggc tctcagtaan                                      30

<210> SEQ ID NO 6
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 6
acactgtcca agtgatgaca tcaattggcn                                      30

<210> SEQ ID NO 7
<211> LENGTH: 59
<212> TYPE: DNA
<213> ORGANISM: Homo sapiens

<400> SEQUENCE: 7
ctgctcactg ctaatggggt tatgcggtta caagggcgtg catcatttcg cacacccag      59

<210> SEQ ID NO 8
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 8
ctgctcactg ctaatggggt tatgcggttn                                      30

<210> SEQ ID NO 9
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 9
ctgggtgtgc gaaatgatgc acgcccttgn                                      30

<210> SEQ ID NO 10
<211> LENGTH: 59
<212> TYPE: DNA
<213> ORGANISM: Homo sapiens
```

-continued

<400> SEQUENCE: 10
ctgctcactg ctaatggggt tatgcggttt caagggcgtg catcatttcg cacacccag    59

<210> SEQ ID NO 11
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 11
ctgctcactg ctaatggggt tatgcggttn                                    30

<210> SEQ ID NO 12
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a ddA

<400> SEQUENCE: 12
ctgggtgtgc gaaatgatgc acgcccttgn                                    30

<210> SEQ ID NO 13
<211> LENGTH: 64
<212> TYPE: DNA
<213> ORGANISM: Homo sapiens

<400> SEQUENCE: 13
agttaaaatt cccgtcgcta tcaaggaacc gaaagccaac aaggaaatcc tcgatgtgag    60
tttc                                                                64

<210> SEQ ID NO 14
<211> LENGTH: 64
<212> TYPE: DNA
<213> ORGANISM: Homo sapiens

<400> SEQUENCE: 14
agtgaacatt cccgtcgcta tcaaggaacc gaaagccaac aaggaaatcc tcgatgtgag    60
tttc                                                                64

<210> SEQ ID NO 15
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a ddC

<400> SEQUENCE: 15
agtgaacatt cccgtcgcta tcaaggaacn                                    30

<210> SEQ ID NO 16
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

```
<400> SEQUENCE: 16
gaaactcaca tcgaggattt ccttgttggn                                    30

<210> SEQ ID NO 17
<211> LENGTH: 67
<212> TYPE: DNA
<213> ORGANISM: Homo sapiens

<400> SEQUENCE: 17
agttaaaatt cccgtcgcta tcaaggaatc tccgaaagcc aacaaggaaa tcctcgatgt   60
gagtttc                                                             67

<210> SEQ ID NO 18
<211> LENGTH: 67
<212> TYPE: DNA
<213> ORGANISM: Homo sapiens

<400> SEQUENCE: 18
aggtacaatt cccgtcgcta tcaaggaatc tccgaaagcc aacaaggaaa tcctcgatgt   60
gagtttc                                                             67

<210> SEQ ID NO 19
<211> LENGTH: 31
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is ddT

<400> SEQUENCE: 19
aggtacaatt cccgtcgcta tcaaggaatc n                                  31

<210> SEQ ID NO 20
<211> LENGTH: 55
<212> TYPE: DNA
<213> ORGANISM: Homo sapiens

<400> SEQUENCE: 20
actgaattca aaaagatcaa agtgctgagc tccggtgcgt tcggcacggt gtata        55

<210> SEQ ID NO 21
<211> LENGTH: 55
<212> TYPE: DNA
<213> ORGANISM: Homo sapiens

<400> SEQUENCE: 21
actgcattca aaaagatcaa agtgctgagc tccggtgcgt tcggcactgt gtata        55

<210> SEQ ID NO 22
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 22
actgcattca aaaagatcaa agtgctgn                                      28

<210> SEQ ID NO 23
```

```
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 23
tatacacagt gccgaacgca ccggagcn                               28

<210> SEQ ID NO 24
<211> LENGTH: 55
<212> TYPE: DNA
<213> ORGANISM: Homo sapiens

<400> SEQUENCE: 24
actgaattca aaagatcaa agtgctgtgc tccggtgcgt tcggcacggt gtata     55

<210> SEQ ID NO 25
<211> LENGTH: 55
<212> TYPE: DNA
<213> ORGANISM: Homo sapiens

<400> SEQUENCE: 25
actgaagtca aaagatcaa agtgctgtgc tccggtgcgt tcggcaaggt gtata     55

<210> SEQ ID NO 26
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 26
actgaagtca aaagatcaa agtgctgn                                28

<210> SEQ ID NO 27
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 27 tataccctt gccgaacgca ccggagcn                                28

<210> SEQ ID NO 28
<211> LENGTH: 55
<212> TYPE: DNA
<213> ORGANISM: Homo sapiens

<400> SEQUENCE: 28
ctgaattcaa aaagatcaaa gtgctggcct ccggtgcgtt cggcacggtg tataa    55

<210> SEQ ID NO 29
<211> LENGTH: 55
<212> TYPE: DNA
<213> ORGANISM: Homo sapiens

<400> SEQUENCE: 29
ctgaatgcaa aaagatcaaa gtgctggcct ccggtgcgtt cggcacgatg tataa    55
```

```
<210> SEQ ID NO 30
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddC

<400> SEQUENCE: 30
ctgaatgcaa aaagatcaaa gtgctggn                                   28

<210> SEQ ID NO 31
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddG

<400> SEQUENCE: 31
ttatacaacg tgccgaacgc accggagn                                   28

<210> SEQ ID NO 32
<211> LENGTH: 59
<212> TYPE: DNA
<213> ORGANISM: Homo sapiens

<400> SEQUENCE: 32
ctgaatataa acttgtggta gttggagctc gtggcgtagg caagagtgcc ttgacgata   59

<210> SEQ ID NO 33
<211> LENGTH: 59
<212> TYPE: DNA
<213> ORGANISM: Homo sapiens

<400> SEQUENCE: 33
ctgactataa acttgtggta gttggagctc gtggcgtagg caagagtgca ttgacgata   59

<210> SEQ ID NO 34
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 34
ctgactataa acttgtggta gttggagctn                                  30

<210> SEQ ID NO 35
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 35
tatcgtcaat gcactcttgc ctacgccacn                                  30

<210> SEQ ID NO 36
```

<210> SEQ ID NO 36
<211> LENGTH: 59
<212> TYPE: DNA
<213> ORGANISM: Homo sapiens

<400> SEQUENCE: 36
ctgaatataa acttgtggta gttggagctt gtggcgtagg caagagtgcc ttgacgata    59

<210> SEQ ID NO 37
<211> LENGTH: 59
<212> TYPE: DNA
<213> ORGANISM: Homo sapiens

<400> SEQUENCE: 37
ctgaatctaa acttgtggta gttggagctt gtggcgtagg caagagtgcc tttacgata    59

<210> SEQ ID NO 38
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 38
ctgaatctaa acttgtggta gttggagctn                                    30

<210> SEQ ID NO 39
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 39
tatcgtaaag gcactcttgc ctacgccacn                                    30

<210> SEQ ID NO 40
<211> LENGTH: 59
<212> TYPE: DNA
<213> ORGANISM: Homo sapiens

<400> SEQUENCE: 40
ctgaatataa acttgtggta gttggagcta gtggcgtagg caagagtgcc ttgacgata    59

<210> SEQ ID NO 41
<211> LENGTH: 59
<212> TYPE: DNA
<213> ORGANISM: Homo sapiens

<400> SEQUENCE: 41
ctgaatatca acttgtggta gttggagcta gtggcgtagg caagagtgcc ttgtcgata    59

<210> SEQ ID NO 42
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 42
ctgaatatca acttgtggta gttggagctn                                    30

```
<210> SEQ ID NO 43
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 43
tgaagataaa cttgtggtag ttggagctgn                                30

<210> SEQ ID NO 44
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 44
tgaatagaaa cttgtggtag ttggagctgn                                30

<210> SEQ ID NO 45
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 45
gtatcgtcat ggcactcttg cctacgccan                                30

<210> SEQ ID NO 46
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 46
tgaatagaaa cttgtggtag ttggagctgn                                30

<210> SEQ ID NO 47
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 47
gtatcgacaa ggcactcttg cctacgccan                                30

<210> SEQ ID NO 48
<211> LENGTH: 30
<212> TYPE: DNA
<213> ORGANISM: Homo sapiens
<220> FEATURE:
<221> NAME/KEY: misc_feature
<222> LOCATION: (30)..(30)
```

<223> OTHER INFORMATION: n is ddT

<400> SEQUENCE: 48
tgaatataga cttgtggtag ttggagctgn                                          30

<210> SEQ ID NO 49
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 49
gtatagtcaa ggcactcttg cctacgccan                                          30

<210> SEQ ID NO 50
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 50
atataacctt gtggtagttg gagctggtgn                                          30

<210> SEQ ID NO 51
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 51
gctgtaacgt caaggcactc ttgcctacgn                                          30

<210> SEQ ID NO 52
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 52
gcagcatgtc aagatcacag attttgggcn                                          30

<210> SEQ ID NO 53
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 53
ctttctcttc cgcacccagc agtttggccn                                          30

<210> SEQ ID NO 54
<211> LENGTH: 30

```
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 54
caagatcaca gattttgggc tggccaaacn                                          30

<210> SEQ ID NO 55
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 55
catggtattc tttctcttcc gcacccagcn                                          30

<210> SEQ ID NO 56
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 56
ctgcctcacc tccaccgtgc agctcatcan                                          30

<210> SEQ ID NO 57
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddG

<400> SEQUENCE: 57
cggacatagt ccaggaggca gccgaagn                                            28

<210> SEQ ID NO 58
<211> LENGTH: 32
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is ddC

<400> SEQUENCE: 58
gagacagtta aaattcccgt cgctatcaaa an                                       32

<210> SEQ ID NO 59
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 59
```

-continued

```
aagttaaaag tcccgtcgct atcaaggttn                                30

<210> SEQ ID NO 60
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 60
gaaagttaaa cttcccgtcg ctatcaagan                                30

<210> SEQ ID NO 61
<211> LENGTH: 31
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is ddG

<400> SEQUENCE: 61
agttaaaatg cccgtcgcta tcaaggaatc n                              31

<210> SEQ ID NO 62
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 62
tttgtttgac atactggata cagctggacn                                30

<210> SEQ ID NO 63
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 63
attggtcact catggcactg tactcttctn                                30

<210> SEQ ID NO 64
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 64
gtttgatgga catactggat acagctggan                                30

<210> SEQ ID NO 65
<211> LENGTH: 30
<212> TYPE: DNA
<213> ORGANISM: Homo sapiens
<220> FEATURE:
<221> NAME/KEY: misc_feature
```

<222> LOCATION: (30)..(30)
<223> OTHER INFORMATION: n is ddT

<400> SEQUENCE: 65
ttggtctcac atggcactgt actcttcttn        30

<210> SEQ ID NO 66
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 66
agtacaaaca ggtggtggtt ggagcagn        28

<210> SEQ ID NO 67
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 67
attgtcattg cgcttttccc aacaccan        28

<210> SEQ ID NO 68
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 68
acaaacttgt ggtggttgga gcaggtgn        28

<210> SEQ ID NO 69
<211> LENGTH: 29
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is ddT

<400> SEQUENCE: 69
ctggattgac agtgcgcttt tcccaacan        29

<210> SEQ ID NO 70
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 70
gagtacacac tggtggtggt tggagcan        28

<210> SEQ ID NO 71

```
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 71
ttgtcagagc gctttttccca acaccacn                                             28

<210> SEQ ID NO 72
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 72
tttgtaggac atactggata cagctggacn                                            30

<210> SEQ ID NO 73
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 73
attggtctat catggcactg tactcttctn                                            30

<210> SEQ ID NO 74
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n id ddT

<400> SEQUENCE: 74
acaaactgtt ggtggttgga gcaggtgn                                              28

<210> SEQ ID NO 75
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 75
tggatggtca gtgcgctttt cccaacan                                              28

<210> SEQ ID NO 76
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddC

<400> SEQUENCE: 76
```
tacaaaatgg tggtggttgg agcaggtn                                              28

<210> SEQ ID NO 77
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddG

<400> SEQUENCE: 77
ggattgtccg tgcgcttttc ccaacacn                                              28

<210> SEQ ID NO 78
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 78
ttgttggtca tactggatac agctggacan                                            30

<210> SEQ ID NO 79
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 79
tattggtatc tcatggcact gtactcttcn                                            30

<210> SEQ ID NO 80
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 80
gagtacaatc tggtggtggt tggagcan                                              28

<210> SEQ ID NO 81
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 81
ttgtaagtgc gcttttccca acaccacn                                              28

<210> SEQ ID NO 82
<211> LENGTH: 30
<212> TYPE: DNA
<213> ORGANISM: Homo sapiens
<220> FEATURE:

<220> FEATURE:
<221> NAME/KEY: misc_feature
<222> LOCATION: (30)..(30)
<223> OTHER INFORMATION: n is ddC

<400> SEQUENCE: 82
ttgttggaaa tactggatac agctggacan                                           30

<210> SEQ ID NO 83
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 83
tattgttctc tcatggcact gtactcttcn                                           30

<210> SEQ ID NO 84
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 84
tacaaactgg aggtggttgg agcaggtn                                             28

<210> SEQ ID NO 85
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 85
ggattttcag tgcgcttttc ccaacacn                                             28

<210> SEQ ID NO 86
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 86
tttgttgtac atactggata cagctggacn                                           30

<210> SEQ ID NO 87
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 87
attggactct catggcactg tactcttctn                                           30

```
<210> SEQ ID NO 88
<211> LENGTH: 31
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is ddC

<400> SEQUENCE: 88
cagtaaaaat aggtgatttt ggtctagcta n                                        31

<210> SEQ ID NO 89
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 89
actgatggga cccactccat cgagatttcn                                          30
```